United States Patent
Parry et al.

(10) Patent No.: US 9,119,833 B2
(45) Date of Patent: Sep. 1, 2015

(54) ADMINISTRATION OF RELAXIN TO TREAT NEPHROGENIC DISEASES OF WATER IMBALANCE INVOLVING AQUAPORIN-4

(71) Applicants: Laura Parry, Coburg (AU); Kirk Conrad, Gainesville, FL (US)

(72) Inventors: Laura Parry, Coburg (AU); Kirk Conrad, Gainesville, FL (US)

(73) Assignees: University of Melbourne, Victoria (AU); University of Florida Research Foundation, Inc., Gainesville, FL (US)

( * ) Notice: Subject to any disclaimer, the term of this patent is extended or adjusted under 35 U.S.C. 154(b) by 0 days.

(21) Appl. No.: 14/074,759

(22) Filed: Nov. 8, 2013

(65) Prior Publication Data

US 2014/0066377 A1    Mar. 6, 2014

Related U.S. Application Data

(63) Continuation of application No. 13/582,478, filed as application No. PCT/US2011/027859 on Mar. 10, 2011, now abandoned.

(60) Provisional application No. 61/339,981, filed on Mar. 10, 2010, provisional application No. 61/340,349, filed on Mar. 15, 2010.

(51) Int. Cl.
   *A61K 38/00* (2006.01)
   *A61P 13/12* (2006.01)
   *A61K 38/22* (2006.01)

(52) U.S. Cl.
   CPC .................................. *A61K 38/2221* (2013.01)

(58) Field of Classification Search
   None
   See application file for complete search history.

(56) References Cited

U.S. PATENT DOCUMENTS

| 4,686,103 A | 8/1987 | Anderson |
| 5,945,402 A | 8/1999 | Cipolla |
| 5,952,296 A | 9/1999 | Bigazzi |
| 6,048,544 A | 4/2000 | Yue |

FOREIGN PATENT DOCUMENTS

| GB | 2459983 | 11/2009 |
| WO | 01/58468 A1 | 8/2001 |
| WO | WO 03/00242 | 1/2003 |
| WO | 2009/140657 | 11/2009 |

OTHER PUBLICATIONS

Parry L. et al. Endocrine. 8(3):317-322, Jun. 1998.*

Parry Laura J et al., "Relaxin Increases Hyaluronan Synthase 2, Hyaluronan and Aquaporin 3 in the Cervix of Pregnant Mice", Reproductive Sciences, Sage Publications Inc., vol. 17, No. 3, p. 256A, 2010.
Gavino E S and Furst D E , "Recombinant relaxin: a review of pharmacology and potential therapeutic use", Biodrugs: Clinical Immunotherapeutics, Biopharmaceuticals and Gene Therapy, ADIS International, FR, vol. 15, No. 9, pp. 609-614, 2001.
Koyama, Yutaka et al., Decreases in rat brain aquaporin-4 expression following intracerebroventricular administration of an endothelin ETB receptor agonist, Neuroscience Letters 469, pp. 343-347, 2010.
Wintour, "Water channels and Urea Transporters", Clinical and Experimental Pharmacology and Physiology (1997) 24, 1-9, 1997.
Wilson et al, "Effects of exogenous relaxin on oxytocin and vasopressin release and the intramammary pressure response to central hyperosmotic challenge", Journal of Endocrinology (1994) 141, 75-80, 1994.
Soh et al Abstract, "Relaxin Regulates Aquaporin Expression in the Cervix of late Pregnant Mice", Reproduction, Fertility and Development, vol. 22 SRB abstracts (supplement) 2010.
Schrier, "Body Water Homeostasis: Clinical Disorders of Urinary Dilution and Concentration", J Am Soc Nephrol 17: 1820-1832, 2006.
Parry et al, "Mechanism of the Haemotensive Action of Porcine Relaxin in Anaesthetized Rats", Journal of Neuroendocrinology, vol. 2, No. I, 53-58, 1990.
Parry et al, "Central Angiotensin Partially Mediates the Pressor Action of Relaxin in Anesthetized Rats", Endocinology, vol. 129, No. 1, 47-52, 1991.
Parry et al, "The Cardiovascular Effects of Porcine Relaxin in Brattleboro Rats", Endocrine, vol. 8, No. 3, 317-233, Jun. 1998.
Hayashi et al, "Expression and Distribution of Aquaporin of Collecting Duct Are Regulated by Vasopressin V2 Receptor in Rat Kidney", The American Society for Clinical Investigation, Inc.,vol. 94, Nov. 1994, 1778-1783.
Bouley et al, "Nitric oxide and atrial natriuretic factor stimulate cGMP-dependent membrane insertion of aquaporin 2 in renal epithelial cells", The Journal of Clinical Investigation, Nov. 2000, vol. 106, No. 9, 1115-1126.
Bekhemia et al, "Pathophysiology of water and sodium retention: edematous states with normal kidney function", Current Opinion in Pharmacology 2006, 6:202-207.
Anderson et al, "Utilization of Different Aquaporin Water Channels in the Mouse Cervix during Pregnancy and Parturition and in Models of Preterm and Delayed Cervical Ripening", Endocrinology 147(1):130-140, 2006.
Reproductive Sciences, 2010, 3, 1, V17, N3, P256A,665.
Zador et al., Role of Aquaporin-4 in Cerebral Edema and Stroke, Handbook of Experimental Pharmacology, (190):159-70, 2009.

* cited by examiner

*Primary Examiner* — Robert Landsman
(74) *Attorney, Agent, or Firm* — James Lynch

(57) ABSTRACT

The present disclosure relates to methods of modulating aquaporin channels. Particularly, the disclosure provides methods of modulating aquaporin channels in a tissue of a mammal by administering relaxin.

4 Claims, 11 Drawing Sheets

* significantly (P<0.05) higher versus cortex and medulla

A.

Cortex     Outer medulla     Inner medulla

* significantly (P<0.05) higher versus inner medulla

C=cortex, M=inner medulla, U=uterus (positive control)

A.

B.

C.

* significantly (P<0.05) lower versus control MCAF

* significantly (P<0.05) higher versus saline

ADMINISTRATION OF RELAXIN TO TREAT NEPHROGENIC DISEASES OF WATER IMBALANCE INVOLVING AQUAPORIN-4

This application is a continuation of U.S. application Ser. No. 13/582,478, now abandoned, which was a National Phase application filed under 35 U.S.C. §371 of PCT/US2011/027859 filed on Mar. 10, 2011, which claims the benefit of U.S. Provisional Application No. 61/339,981, filed Mar. 10, 2010, and U.S. Provisional Application No. 61/340,349 filed Mar. 15, 2010, which in their entirety are herein incorporated by reference.

TECHNICAL FIELD

The present disclosure relates to methods of modulating aquaporin channels. Particularly, the disclosure provides methods of modulating aquaporin channels in a tissue of a mammal by administering relaxin.

BACKGROUND

The Aquaporin Family

The aquaporins are a family of small (24-30 kDa) pore-forming integral membrane proteins characterized by six transmembrane helices that selectively allow water or other small uncharged molecules to pass along an osmotic gradient. These proteins form tetramers, with each monomer defining a single pore. The aquaporin protein family was first named after the major intrinsic protein (MIP) of the mammalian lens, which is now designated AQP0. When MIP homologs were eventually shown to function as water channels, the name aquaporin was adopted for the family. The aquaporin family has representatives in all kingdoms, including archaea, eubacteria, fungi, plants and animals. The MIP homologs with exclusive water permeability are referred to as aquaporins, whereas water- and glycerol-permeable homologs are referred to as aquaglyceroporins. In vertebrates, eleven different aquaporins have so far been identified, corresponding to the human proteins AQP0-AQP10. Of these, seven aquaporins (AQP0, AQP1, AQP2, AQP4, AQP5, AQP6, and AQP8) have been characterized as the classical aquaporins that promote water transport in mammals. The other four aquaporins (AQP3, AQP7, AQP9 and AQP10) promote glycerol transport in mammals and have, thus, been assigned to the GLP subfamily. Additional aquaporins have been identified in E. coli, yeast and plants (Kruse et al. (2006) Genome Biology 7(2)(206):1-6).

The first member of the aquaporin family that was extensively described was the channel-like integral membrane protein of the human erythrocyte membrane. This protein was originally known as the 28 kDa protein CHIP28. Based on functional analyses, this protein was later renamed aquaporin-1 (AQP1). Experiments with the primary protein sequence of aquaporin-1 (AQP1) predicted six transmembrane helices (I-VI) connected by five loops (loops A-E). Loops A, C and E are extracellular and loops B and D are intracellular. In addition, the protein comprises two internal tandem repeats, covering roughly the amino- and carboxy-terminal halves of the protein. Each repeat consists of three transmembrane helices and a highly conserved loop following the second transmembrane helix (loops B and E, respectively). This loop includes the conserved signature motif, asparagine-proline-alanine (NPA). Loops B and E form short α helices that fold back into the membrane, with loop B entering the membrane from the cytoplasmic side and loop E from the extracellular side. A seventh transmembrane domain in which the two NPA boxes are orientated 180 degrees to each other is thus formed, creating an aqueous pathway through the proteinaceous pore. Since all aquaporins are structurally related and have highly similar consensus regions, particularly in the pore-forming domains, a similar transport mechanism is likely. The hydrophobic domain created by the loops B and E has been suggested to be involved in substrate specificity and/or size restriction. The pathway through the aquaporin monomer is lined with conserved hydrophobic residues that permit rapid transport of water in the form of a single-file hydrogen-bonded chain of water molecules. The pore contains two constriction sites, i.e., an aromatic region comprising a conserved arginine residue (Arg195) forms the narrowest part of the pore, while the highly conserved NPA motifs form a second filter, where single water molecules interact with the two asparagine side chains. Since there is a direct interaction between water molecules and the NPA motifs, the dipolar water molecule rotates 180 degrees during passage through the pore. Both filter regions build up electrostatic barriers, which prevent the permeation of protons. In human AQP1, a hydrophobic phenylalanine side chain (Phe24) intrudes into the pore and enhances the interaction of single permeating water molecules with the NPA loops. In fact, Phe24 acts as a size-exclusion filter, preventing the passage of larger molecules such as glycerol through AQP1. The water permeabilities for human aquaporins are estimated to be between $0.25 \times 10^{-14}$ cm$^3$/sec for AQP0 and $24 \times 10^{-14}$ cm$^3$/sec for AQP4. However, aquaporins are believed to have different requirements for osmoregulation and transmembrane water movement in different tissues, organs and developmental stages. In mammals, aquaporins are localized in epithelia that need a high rate of water flux, such as the collecting duct of the kidney, the capillaries of the lung, and the secretory cells of the salivary glands. In addition, mammalian aquaporins differ in their transcriptional regulation, post-transcriptional regulation and subcellular distribution (Kruse et al. (supra)).

Edema

Edema is the swelling of tissues that occurs when excessive fluid accumulates within those tissues. Edema is a symptom of systemic diseases, i.e., diseases that affect the various organ systems of the body. It may be caused by local conditions involving just the affected extremities. In peripheral edema, the swelling is the result of the accumulation of too much fluid under the skin in the spaces within the tissues, also known as the interstitial spaces or interstitium made up of connective tissue. Most bodily fluids that are found outside of the cells are normally stored in the blood vessels and the interstitial spaces. In various diseases and under certain conditions, excess fluid can accumulate in either one or both of these compartments. The most common local conditions that cause edema are varicose veins and thrombophlebitis, i.e., inflammation of the veins of the deep veins of the legs. These conditions can lead to inadequate pumping of the blood by the veins which in turn leads to venous insufficiency. The resulting increased back-pressure in the veins forces fluid to stay in the extremities, particularly in the ankles and feet. The excess fluid then leaks into the interstitial spaces, causing edema. Although, the swelling may be limited to specific areas like the lower limbs, it may also spread over large areas of the body. Systemic edema is most commonly associated with heart, liver and kidney diseases. It occurs primarily because the body retains too much salt, i.e., sodium chloride. The excess salt causes the body to retain water. This water then leaks into the interstitial spaces, where it appears as edema.

In general, edema is classified by the location of the swelling tissue. There are numerous examples such as peripheral edema which is mainly swelling of the lower limbs; pulmonary edema which is accumulation of fluid in the lungs; periorbital edema which is swelling around the eyes; ocular edema which is fluid retention in the cornea; cerebral edema which is swelling of brain tissue; ascites (excess fluid in the abdomen); massive edema (i.e., anasarca) which is swelling that covers a large part of the body; and the like. Other body locations that may become swollen include the gums, lymph glands, face, abdomen, breasts, scrotum, liver, and the joints. The signs and symptoms of edema vary depending on the location of the tissue and the extent of the swelling. For many types of edema, fluid builds up under the skin, causing swelling and making the overlying area stretched and shiny. Edema can be pitting or non-pitting. In pitting edema, pressing a finger against a swollen area and then removing it leaves an indentation that slowly disappears. When edema becomes more severe, the tissue swells so much that it cannot be displaced, and no indentation is left in the skin after applying pressure such as in non-pitting edema. Edema that occurs over pressure points over bony areas of the body can develop into serious sores or ulcers, especially in bedridden patients.

Edema is also known to be itself a symptom associated with several different underlying diseases such as kidney, liver, and heart disease. Hence, edema can be a long-term and progressive manifestation of a disorder with serious consequences. For example, pulmonary edema can be a complication of heart failure. As the heart pumps less efficiently, fluid leaks out of the veins in the lungs and fills the air sacs or alveoli, making it difficult to breathe. Pulmonary edema can become life-threatening, and if left untreated, can rapidly lead to death. Symptoms of pulmonary edema include shortness of breath, grunting while breathing, a crackling or rattling noise in the lungs noticeable with a stethoscope (rales), wheezing, anxiety, restlessness, coughing, excessive sweating, abnormally pale skin (pallor), abnormal heartbeat or rhythm, and chest pain. However, even patients with less severe heart failure that may not lead to pulmonary edema can still experience serious swelling in their lower limbs. Edema can also be caused by chronic lung disease. Severe chronic lung disease, such as chronic obstructive pulmonary disease (COPD), emphysema, or chronic bronchitis can restrict blood flow in the blood vessels in the lungs. The restricted blood flow creates pressure in the blood vessels that can back up throughout the rest of the circulatory system. This pressure, in turn, causes fluid to leak into surrounding tissues, causing swelling, i.e., edema, such as in the legs and feet.

Additional causes of edema are varicose veins (as a result of blood pooling in the lower legs); long sitting or standing as in orthostatic edema (e.g., as a result of hot weather, long plane and automobile rides); certain medications (e.g., oral contraceptives containing estrogen or progesterone, blood pressure medications, certain antidepressants, oral corticosteroids, testosterone); pregnancy (as a result of increased blood pressure in the lower limbs which can be due to preeclampsia); allergic reactions; sunburns; malnutrition, injury or trauma; blockages in the lymphatic system (e.g., caused by infection, inflammation, or cancer), exposure to high altitude as in high altitude edema; hormonal changes associated with menstruation in some women; nephrotic syndrome (in which damaged kidneys lose excess protein in the urine leading to severe swelling in the ankles); and severe liver disease (leading to cirrhosis and excess ankle swelling).

Since edema is often a symptom of another underlying condition, the risk factors for edema are the same as those for the underlying conditions. As such, the same risk factors as in kidney, liver, heart, and lung disease apply to edema. For example, smoking is a major risk factor for chronic lung disease, high blood pressure is a major risk factor for heart disease, and obesity is a major risk factor for both heart disease and diabetes. All of these risk factors also increase a subject's risk of developing edema. In addition, edema occurs more commonly in individuals with older age because many of the underlying causes of edema occur more frequently in older populations.

BRIEF SUMMARY OF PREFERRED EMBODIMENTS

One aspect of the disclosure provides a method of modulating an aquaporin channel in a mammal, including administering to the mammal a relaxin in an amount effective to modify aquaporin expression in a tissue of the mammal. The aquaporin expression can be aquaporin gene expression and/or aquaporin protein expression. Both aquaporin gene and protein expression can be up-regulated or down-regulated. In one embodiment, the aquaporin channel gene includes, but is not limited to, aquaporin-0 gene (aqp0), aquaporin-1 gene (aqp1), aquaporin-2 gene (aqp2), aquaporin-3 gene (aqp3), aquaporin-4 gene (aqp4), aquaporin-5 gene (aqp5), aquaporin-6 gene (aqp6), aquaporin-7 gene (aqp7), aquaporin-8 gene (aqp8), aquaporin-9 gene (aqp9) and aquaporin-10 gene (aqp10). In another embodiment, the aquaporin channel includes, but is not limited to, aquaporin-0 (AQP0), aquaporin-1 (AQP1), aquaporin-2 (AQP2), aquaporin-3 (AQP3), aquaporin-4 (AQP4), aquaporin-5 (AQP5), aquaporin-6 (AQP6), aquaporin-7 (AQP7), aquaporin-8 (AQP8), aquaporin-9 (AQP9) and aquaporin-10 (AQP10). In yet another embodiment, the aquaporin channel gene includes, but is not limited to, aquaporin-1 gene (aqp1), aquaporin-2 gene (aqp2), aquaporin-3 gene (aqp3), aquaporin-4 gene (aqp4), and aquaporin-5 gene (aqp5). In yet another embodiment, the aquaporin channel includes, but is not limited to, aquaporin-1 (AQP1), aquaporin-2 (AQP2), aquaporin-3 (AQP3), aquaporin-4 (AQP4), and aquaporin-5 (AQP5).

Another aspect of the disclosure provides a method of modulating an aquaporin channel in a mammal, including administering relaxin to the mammal in an amount effective to modify aquaporin expression in a tissue of the mammal, wherein the aquaporin expression includes one or more of aquaporin genes aqp2, aqp3, aqp4 and aqp5 and/or aquaporin proteins AQP2, AQP3, AQP4 and AQP5. In one embodiment, aqp3 is up-regulated in the cervix. In another embodiment, aqp5 is down-regulated in the cervix. In another embodiment, AQP3 is up-regulated in the cervix. In another embodiment, AQP5 is down-regulated in the cervix. In another embodiment, aqp2 and aqp4 are up-regulated in the kidney. In still another embodiment, AQP2 and AQP4 are up-regulated in the kidney.

Another aspect of the disclosure provides a method of modulating an aquaporin channel in a mammal, including administering relaxin to the mammal in an amount effective to modify aquaporin expression in a tissue of the mammal, wherein the tissue includes, but is not limited to, organ tissue, muscle tissue, epithelial tissue and endothelial tissue. In one embodiment, the organ tissue includes, but is not limited to, brain tissue, kidney tissue, lung tissue, and reproductive tissue. In another embodiment, the mammal is a human.

Further encompassed by the disclosure is a method of modulating an aquaporin channel in a mammal by administering relaxin to the mammal. In one embodiment, relaxin modulates aquaporin gene expression. In another embodiment, relaxin modulates aquaporin protein expression. In yet another embodiment, aquaporin gene includes, but is not limited to, aquaporin-1 gene (aqp1), aquaporin-2 gene (aqp2), aquaporin-3 gene (aqp3), aquaporin-4 gene (aqp4), and aquaporin-5 gene (aqp5). In yet another embodiment, aquaporin protein includes, but is not limited to, aquaporin-1 (AQP1), aquaporin-2 (AQP2), aquaporin-3 (AQP3), aquaporin-4 (AQP4), and aquaporin-5 (AQP5).

Another aspect of the disclosure provides a method of treating edema. The method includes administering a pharmaceutically active relaxin to a human subject in an amount effective in reducing fluid accumulation associated with edema in a tissue in the human subject. Relaxin is provided in the form of a pharmaceutical formulation in order to treat edema. Relaxin employed in the pharmaceutical formulations of the disclosure can be, for example, synthetic or recombinant relaxin, or a pharmaceutically effective relaxin agonist. In one embodiment of the disclosure, relaxin is H1 human relaxin. In another embodiment, relaxin is H2 human relaxin. In yet another embodiment, relaxin is H3 human relaxin. In a further embodiment, relaxin is synthetic or recombinant human relaxin, or a pharmaceutically effective relaxin agonist. Thus, the subject can be treated for edema with a pharmaceutical formulation of synthetic or recombinant human relaxin or relaxin agonist or any agent that has relaxin-like activity. In one embodiment of the disclosure, the subject is treated with synthetic human relaxin. In another embodiment, the subject is treated with recombinant human relaxin. In yet another embodiment, the subject is treated with a pharmaceutically effective relaxin agonist. Relaxin can be administered to the human subject through a number of different routes, including but not limited to, intravenously, subcutaneously, intramuscularly, sublingually, intranasally, intracerebrally, intracerebroventricularly, topically, intravitrealy and via inhalation. Such routes of administration include, but are not limited to, intravenous infusion, intravenous bolus, subcutaneous infusion, subcutaneous bolus, subcutaneous pump, intravitreal injection, and topical eye drops. More specifically, the pharmaceutical formulation of relaxin or relaxin agonist can be administered to the subject in an amount in a range of about 10 to 1000 µg/kg of subject body weight per day. In one embodiment, relaxin is administered at an intravenous or subcutaneous infusion rate in a range of about 3 µg/kg/day to about 150 µg/kg/day. In another embodiment, relaxin is administered at an intravenous or subcutaneous infusion rate in a range of about 30 µg/kg/day. As such, relaxin is administered to the subject so as to maintain a serum concentration of relaxin of about 1 to about 500 ng/ml. In one embodiment, relaxin is administered in order to maintain a serum concentration of about 1 ng/ml to about 100 ng/ml. In another embodiment, relaxin is administered in order to maintain a serum concentration of about 10 ng/ml. The reduction of fluid accumulation associated with edema in the tissue in the human subject can be measurable within about 24 hours after the onset of treatment with relaxin compared to treatment with placebo. In some circumstances, a reduction of fluid accumulation associated with edema in the tissue in the human subject can be measurable as early as within about 4 to 6 hours after the onset of treatment with relaxin compared to treatment with placebo.

Another aspect of the disclosure provides a method of treating edema in the brain of a human subject. The method includes administering a pharmaceutically active relaxin to a human subject in an amount effective to reduce fluid accumulation associated with edema in a brain tissue in the human subject. The brain edema may affect one or more areas of the brain. In one embodiment, the brain edema is cerebral edema. Other forms of brain edema are also encompassed. In order to treat brain edema, relaxin can be, for example, administered intravenously, subcutaneously, intracerebrally, or intracerebroventricularly. As such, affected subjects can be administered relaxin, for example, via intravenous infusion, via intravenous bolus, via subcutaneous infusion, or via subcutaneous bolus. The type of relaxin administration depends on the condition of the patient and circumstances involved. In one embodiment, relaxin is administered in order to maintain a serum concentration of about 1 ng/ml to about 100 ng/ml in the human subject. In another embodiment, relaxin is administered in order to maintain a serum concentration of about 10 ng/ml in the human subject. In another embodiment, relaxin is administered at an intravenous or subcutaneous infusion rate in a range of about 3 µg/kg/day to about 150 µg/kg/day. In yet another embodiment, relaxin is administered at an intravenous or subcutaneous infusion rate in a range of about 30 µg/kg/day. Relaxin can be administered at an intravenous or subcutaneous bolus in a range of about 3 µg/kg/day to about 150 µg/kg/day. In still another embodiment, relaxin is administered at an intravenous or subcutaneous bolus in a range of about 30 µg/kg/day. The reduction of fluid accumulation associated with edema in the brain tissue in the human subject can be measurable within about 24 hours after the onset of treatment with relaxin compared to treatment with placebo. In some circumstances, a reduction of fluid accumulation associated with edema in the brain tissue in the human subject can be measurable as early as within about 4 to 6 hours after the onset of treatment with relaxin compared to treatment with placebo. Depending on the condition of the patient and the severity of the edema, a reduction of fluid accumulation may be measurable such that an improvement in the edema can be noted at the appropriate time points. Such a reduction in fluid accumulation can be measured via Magnetic Resonance Imaging (MRI) or other techniques that are available to physicians. In addition, a reduction in fluid accumulation in the brain can be linked to improvements in patient behavior such as improvements in coordination, levels of consciousness and numbness, as well as reduction in dizziness, nausea and memory loss.

Another aspect of the disclosure provides a method for treating edema, including administering to a human subject a pharmaceutically active relaxin in an amount effective to modify aquaporin expression in a brain tissue in a human subject. Such a method will include, but is not limited to, cerebral edema, including vasogenic and cytotoxic edema.

The disclosure further contemplates a method for treating edema, including administering to a human subject a pharmaceutically active relaxin in an amount effective to reduce fluid accumulation associated with edema in a corneal tissue in said human subject. In one embodiment, the edema is ocular edema. In order to treat ocular edema, relaxin can be administered intravenously, subcutaneously, topically, or intravitrealy. The intravenous administration may occur via intravenous infusion or intravenous bolus. The subcutaneous administration may occur via subcutaneous infusion or subcutaneous bolus. The topical administration can occur via topical eye drops. The intravitreal administration can occur via injection, for example, injection into the eye. In one embodiment, relaxin is administered in order to maintain a serum concentration of about 1 ng/ml to about 100 ng/ml in the human subject. In another embodiment, relaxin is administered in order to maintain a serum concentration of about 10 ng/ml in the human subject. In another embodiment, relaxin is administered at an intravenous or subcutaneous infusion rate in a range of about 3 µg/kg/day to about 150 µg/kg/day. In yet another embodiment, relaxin is administered at an intravenous or subcutaneous infusion rate in a range of about 30 µg/kg/day. In still another embodiment, relaxin is administered at an intravenous or subcutaneous bolus in a range of about 3 μg/kg/day to about 150 μg/kg/day. Further encompassed is a relaxin administration at an intravenous or subcutaneous bolus in a range of about 30 μg/kg/day. The reduction of fluid accumulation associated with edema in the corneal tissue in the human subject can be measurable within about 24 hours after the onset of treatment with relaxin compared to treatment with placebo. In some patients, a reduction of fluid accumulation associated with edema in the corneal tissue in the human subject can be measurable as early as within about 4 to 6 hours after the onset of treatment with relaxin compared to treatment with placebo. Depending on the condition of the patient and the severity of the ocular edema, a reduction of fluid accumulation may be measurable such that an improvement in the edema can be noted at the appropriate time points. Such a reduction in fluid accumulation can be measured via Magnetic Resonance Imaging (MRI), swelling and/or inflammation of the cornea via ocular evaluation by a physician, a reduction in distorted vision, as well as a reduction in eye discomfort and photophobia.

Another aspect of the disclosure provides a method for treating edema, including administering a pharmaceutically active relaxin to a human subject in an amount effective to modify aquaporin expression in a corneal tissue in the human subject. Such a method includes, but is not limited to, ocular edema.

The disclosure further contemplates treating edema, including administering a pharmaceutically active relaxin to a human subject in an amount effective to reduce fluid accumulation associated with edema in a lung tissue in the human subject. In one embodiment, the edema is pulmonary edema. In order to treat pulmonary edema or any edema occurring in the lung, relaxin can be administered intravenously or subcutaneously. The intravenous administration may occur via intravenous infusion or intravenous bolus. The subcutaneous administration may occur via subcutaneous infusion or subcutaneous bolus. In one embodiment, relaxin is administered in order to maintain a serum concentration of about 1 ng/ml to about 100 ng/ml in the human subject. In another embodiment, relaxin is administered in order to maintain a serum concentration of about 10 ng/ml in the human subject. In another embodiment, relaxin is administered at an intravenous or subcutaneous infusion rate in a range of about 3 μg/kg/day to about 150 μg/kg/day. In yet another embodiment, relaxin is administered at an intravenous or subcutaneous infusion rate in a range of about 30 μg/kg/day. In still another embodiment, relaxin is administered at an intravenous or subcutaneous bolus in a range of about 3 μg/kg/day to about 150 μg/kg/day. Further encompassed is a relaxin administration at an intravenous or subcutaneous bolus in a range of about 30 μg/kg/day. The reduction of fluid accumulation associated with edema in the lung tissue in the human subject can be measurable within about 24 hours after the onset of treatment with relaxin compared to treatment with placebo. In some patients, a reduction of fluid accumulation associated with edema in the lung tissue in the human subject can be measurable as early as within about 4 to 6 hours after the onset of treatment with relaxin compared to treatment with placebo. Depending on the condition of the patient and the severity of the pulmonary edema, a reduction of fluid accumulation may be measurable such that an improvement in the edema can be noted at the appropriate time points. Such a reduction in fluid accumulation can be measured via chest X-ray. In addition, a reduction in fluid accumulation can be linked to patient relief of lung congestion as well as improvements in breathing (via an examination by auscultation to listen to improvements in breathing) and increased oxygen saturation (via measurements of arterial blood gas).

Another aspect of the disclosure provides a method for treating edema, comprising administering to a human subject a pharmaceutically active relaxin in an amount effective to modify aquaporin expression in a lung tissue in the human subject. In one embodiment, the edema is pulmonary edema.

Still, another aspect of the invention provides a method for treating peripheral edema, including administering to a human subject a pharmaceutically active relaxin in an amount effective to reduce fluid accumulation associated with edema in a swollen tissue in the human subject, wherein the swollen tissue includes an area under the skin of the human subject. In one embodiment, the swollen tissue is connective tissue of the skin. Peripheral edema can occur in specific populations of patients such as patient populations that suffer from a particular condition, including congestive heart failure, trauma, alcoholism, altitude sickness, pregnancy, hypertension, or others. In addition, such patients may suffer from liver disease or a specific type of heart condition. In addition, such patients may also suffer from organ failure of one type or another. Peripheral edema can also occur in isolation such as in patients who present with swollen limbs wherein the swelling is not associated with a specific condition and cannot be related to a specific disease or origin. Sometimes, such subjects merely engage in long periods of time sitting or standing without moving (e.g., people in offices who sit behind desks for long periods of time or people working in assembly lines who stand for long periods of time). Relaxin can be used to treat peripheral edema that occurs in isolation or edema that is a symptom of another disease or is related to another disease condition. In order to treat peripheral edema, relaxin can be administered intravenously or subcutaneously. The intravenous administration may occur via intravenous infusion or intravenous bolus. The subcutaneous administration may occur via subcutaneous infusion or subcutaneous bolus. In one embodiment, relaxin is administered in order to maintain a serum concentration of about 1 ng/ml to about 100 ng/ml in the human subject. In another embodiment, relaxin is administered in order to maintain a serum concentration of about 10 ng/ml in the human subject. In another embodiment, relaxin is administered at an intravenous or subcutaneous infusion rate in a range of about 3 μg/kg/day to about 150 μg/kg/day. In yet another embodiment, relaxin is administered at an intravenous or subcutaneous infusion rate in a range of about 30 μg/kg/day. In still another embodiment, relaxin is administered at an intravenous or subcutaneous bolus in a range of about 3 μg/kg/day to about 150 μg/kg/day. Further encompassed is a relaxin administration at an intravenous or subcutaneous bolus in a range of about 30 μg/kg/day. The reduction of fluid accumulation associated with peripheral edema in the swollen tissue in the human subject can be measurable within about 24 hours after the onset of treatment with relaxin compared to treatment with placebo. In some patients, a reduction of fluid accumulation associated with peripheral edema in the swollen tissue in the human subject can be measurable as early as within about 4 to 6 hours after the onset of treatment with relaxin compared to treatment with placebo. Depending on the condition of the patient and the severity of the peripheral edema, a reduction of fluid accumulation may be measurable such that an improvement in the edema can be noted at the appropriate time points. Such a reduction in fluid accumulation can be measured via a reduction in swelling upon physical examination as well as an acute decrease in body weight over 24 to 48 hours. As the patient loses water, the body weight decreases noticeably which, in turn, relates directly to a reduction in edema.

Another aspect of the disclosure provides a method for treating peripheral edema, comprising administering to a human subject a pharmaceutically active relaxin in an amount effective to modify aquaporin expression in a tissue in the human subject. In one embodiment, the tissue is swollen tissue which includes an area under the skin. In another embodiment, the tissue is connective tissue.

The disclosure further encompasses a method for treating systemic edema, including administering to a human subject a pharmaceutically active relaxin in an amount effective to reduce fluid accumulation associated with edema in a tissue in the human subject. The tissue may include, but is not limited to, lung, heart, kidney and liver. Similar to peripheral edema, systemic edema can occur in specific populations of patients such as patient populations that suffer from a particular condition. For example, such patients may suffer from liver disease, a specific type of heart condition, a hypothyroid condition, a lung condition, a kidney disorder, and the like. In addition, such patients may also suffer from organ failure of one type or another. Systemic edema can also occur in a single organ such as in patients who present with cirrhosis and/or ascites and suffer from edema in the liver. Alternatively, systemic edema may occur in more than one organ at the same time. Relaxin can be used to treat systemic edema that occurs in one or multiple organs. In order to treat systemic edema, relaxin can be administered intravenously or subcutaneously. The intravenous administration may occur via intravenous infusion or intravenous bolus. The subcutaneous administration may occur via subcutaneous infusion or subcutaneous bolus. In one embodiment, relaxin is administered in order to maintain a serum concentration of about 1 ng/ml to about 100 ng/ml in the human subject. In another embodiment, relaxin is administered in order to maintain a serum concentration of about 10 ng/ml in the human subject. In another embodiment, relaxin is administered at an intravenous or subcutaneous infusion rate in a range of about 3 µg/kg/day to about 150 µg/kg/day. In yet another embodiment, relaxin is administered at an intravenous or subcutaneous infusion rate in a range of about 30 µg/kg/day. In still another embodiment, relaxin is administered at an intravenous or subcutaneous bolus in a range of about 3 µg/kg/day to about 150 µg/kg/day. Further encompassed is a relaxin administration at an intravenous or subcutaneous bolus in a range of about 30 µg/kg/day. The reduction of fluid accumulation associated with systemic edema in the affected tissue or organ in the human subject can be measurable within about 24 hours after the onset of treatment with relaxin compared to treatment with placebo. In some patients, a reduction of fluid accumulation associated with systemic edema in the affected tissue or organ in the human subject can be measurable as early as within about four to six hours after the onset of treatment with relaxin compared to treatment with placebo. Depending on the condition of the patient and the severity of the systemic edema, a reduction of fluid accumulation may be measurable such that an improvement in the edema can be noted at the appropriate time points. Such a reduction in fluid accumulation can be measured by examining the patient for the appropriate symptom relief or by employing a scan that matches the condition that underlies the edema such as a CT scan or Ultrasound (shows a reduction in abdominal girth and bloating), an MRI (shows a reduction in water content of a specific organ), a chest X-ray (shows a reduction in lung fluid), and Echocardiogram (shows the size of the heart's chambers and other changes in and around the heart).

Another aspect of the disclosure provides a method for treating systemic edema, comprising administering to a human subject a pharmaceutically active relaxin in an amount effective to modify aquaporin expression in a tissue in the human subject. In one embodiment, the tissue is lung, heart, kidney and liver.

Yet another aspect of the invention provides a method for treating edema, comprising administering to an animal a pharmaceutically active relaxin in an amount effective to reduce fluid accumulation associated with edema in a tissue in the animal. In one preferred embodiment, the animal is a dog, a cat, or a horse.

Further contemplated by the present disclosure is a method of treating nephrogenic diabetes insipidus (NDI), including administering to a human subject a pharmaceutically active relaxin in an amount effective to reduce chronic excretion of dilute urine in the human subject. Since patients with NDI suffer from frequent and heavy urination, excessive thirst, and an overall feeling of weakness, a reduction in one or more of these symptoms as a result of relaxin treatment would indicate an improvement in the condition. For example, a reduction in the frequency of urination, a decrease in 24 hour urine volume, a follow-up measurement of urine osmolality, and/or patient relief of intensive thirst could be directly linked to an improvement of NDI via relaxin. As such, relaxin is administered to maintain a serum concentration of about 1 ng/ml to about 100 ng/ml in the human subject. In another embodiment, relaxin is administered in order to maintain a serum concentration of about 10 ng/ml in the human subject. In another embodiment, relaxin is administered at a subcutaneous infusion rate in a range of about 3 µg/kg/day to about 150 µg/kg/day. In yet another embodiment, relaxin is administered at a subcutaneous infusion rate in a range of about 30 µg/kg/day. In addition, relaxin can be administered chronically at various different routs including by intermittent subcutaneous injection or pump. Particularly, relaxin can be administered continuously for at least 24 hours. In a NDI patient, a reduction in dilute urine excretion associated with NDI can be measurable within about 24 hours after the onset of treatment with relaxin compared to treatment with placebo. Alternatively, a reduction in dilute urine excretion associated with NDI in the human subject can be measurable as early as within about 4 to 6 hours after the onset of treatment with relaxin compared to treatment with placebo.

Another aspect of the disclosure provides a method for treating nephrogenic diabetes insipidus (NDI), including administering to a human subject a pharmaceutically active relaxin in an amount effective to modify aquaporin expression and cellular localization in kidney tissue in the human subject. In one embodiment, the aquaporin is aquaporin-2 (AQP2), aquaporin-3 (AQP3), and/or aquaporin-4 (AQP4).

BRIEF DESCRIPTION OF THE FIGURES

The present disclosure is best understood when read in conjunction with the accompanying figures, which serve to illustrate the preferred embodiments. It is understood, however, that the disclosure is not limited to the specific embodiments disclosed in the figures.

FIGS. 6A-B.

FIG. 7A shows RXFP1 protein in cross-sections of the renal tubules in the cortex, outer medulla and inner medulla by immunohistochemistry. FIGS. 7B and 7C show expression of the Rxfp1 gene in the cortex and medulla regions of female and male rats by quantitative-PCR. FIG. 7D shows quantitative protein expression in the cortex and medulla regions by Western blot analysis.

DETAILED DESCRIPTION OF THE EMBODIMENTS

General Overview

Figure 1:
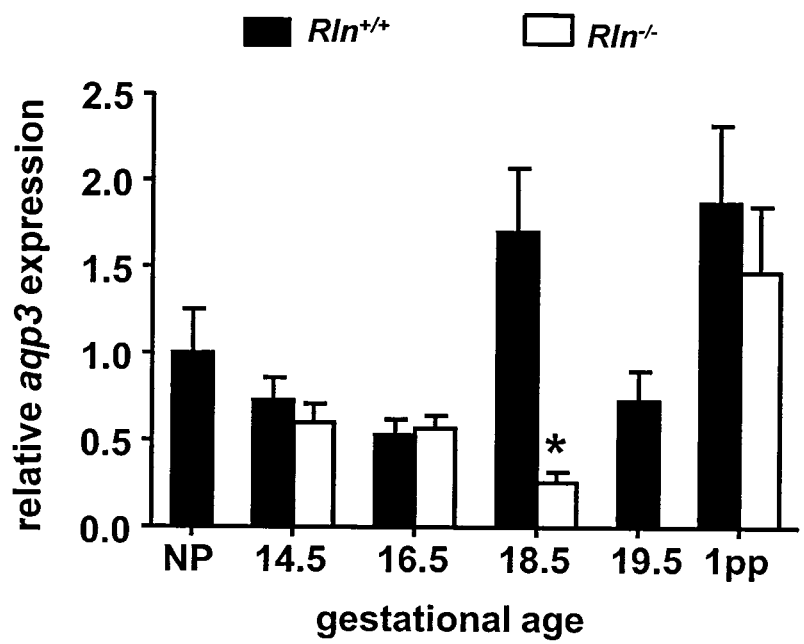
FIG. 1 shows the reduction in aqp3 gene expression in the cervix of late pregnant relaxin deficient (Rln−/−) mice.
Figure 2:
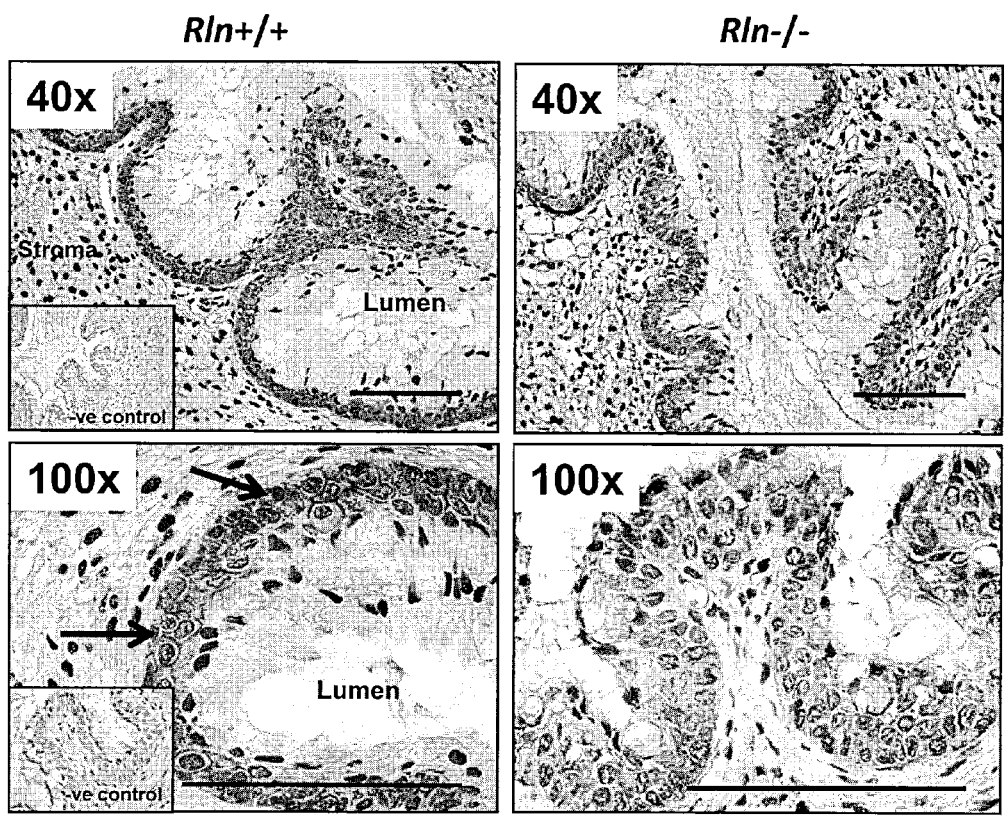
FIG. 2 shows that AQP3 protein is localized predominantly to the basal layer of epithelial cells (see arrows) in the mouse cervix. There is a lower level of AQP3 protein expression in Rln−/− mice compared with wildtype (Rln+/+) mice.

The present disclosure relates to methods of modulating aquaporin channels through the administration of relaxin. Aquaporins are proteins that are embedded in the cell membrane of most cells in order to regulate the flow of water and glycerol in various tissues of the body. The inventors have shown that relaxin is capable of modulating these water channels, i.e., relaxin can up-regulate and/or down-regulate expression of specific aquaporins in specific tissues and/or organs. This in turn affects the flow of water through specific aquaporins in specific tissues and/or organs, and thereby changes the permeability of biological membranes to water, and further alters fluid content of body tissues and/or organs. In case of specific aquaporins, the present inventors have shown that the effect of modifying their gene expression is consistent from one tissue to another. Since aquaporins are expressed in most mammalian tissues and are highly conserved throughout the mammalian system the ability to up- and down-regulate their expression provides a fundamental basis for the understanding of many disease processes. For example, edema is a condition that is the result of excessive water accumulation in tissues and/or organs, thus, relaxin treatment can benefit subjects afflicted with edema and/or symptoms thereof.

More specifically, treatment with human recombinant (H2) relaxin in mice increases aqp3 gene expression and the amount of AQP3 protein in the epithelial cells of the cervix in late pregnancy. This promotes water influx from the lumen of the cervix, across the epithelial cells and increases water content in the stroma tissue to facilitate remodeling of the extracellular matrix. Relaxin treatment can also decrease aquaporins in the same tissue. For example, relaxin decreases aqp5 gene expression and the amount of AQP5 protein in the basal layer of cervical epithelial cells in late pregnancy. In another study, relaxin treatment was shown to increase aqp2 and aqp4 gene expression in the medulla and papilla regions of the kidney in two mammalian species. This action in the kidney promotes movement of water out of the nephron filtrate, across the cells of the nephron and back into the blood, which is necessary to concentrate the urine and reduce plasma osmolality.

Consequently, the present disclosure further relates to methods of reducing edema by administering relaxin to afflicted subjects. Particularly, these methods include administering pharmaceutically active relaxin in an amount effective to reduce the fluid accumulation that is generally associated with edema. Since edema is a common side effect or symptom of many diseases and further a condition that affects the elderly, it is associated with a steadily increasing cost to the health care system. For example, there are numerous forms of edema, including, but not limited to, cerebral edema, ocular edema, pulmonary edema, ascites, hereditary angioedema, peripheral edema, and systemic edema of which all are the result of accumulation of fluid in body tissues and organs. Furthermore, edema is a common condition associated with traumatic injury to the brain and spinal cord such as in brain or cerebral edema. In addition, edema frequently accompanies stroke and it can dramatically complicate the clinical course of brain tumors. Current treatments for brain edema, for example, are limited and include osmotherapy and glucocorticoids. The use of osmotherapy includes administration of hypertonic mannitol in order to help reverse the swelling in the brain. However, this treatment is limited and is often not successful, because osmotherapy shrinks healthy brain tissue along with the damaged area. By the same token, glucocorticoids have not been very successful either in the treatment of most forms of brain edema and have failed entirely in stroke-associated edema. Similarly, surgical decompression is an invasive procedure that often puts the patient at risk. Sadly, these treatments have been used for the last 70 years with very little success. The cost of treatment for traumatic brain injury and associated edema alone exceeds 14 billion USD annually and it is steadily rising. Hence, patient populations afflicted with edema are in need of new therapeutic methods that improve the condition and stabilize the patients without causing serious side effects. Relaxin is a naturally occurring substance that, when administered to subjects with edema, can reduce the fluid accumulation in tissue that is associated with edema without affecting the neighboring tissue. As such, relaxin offers a new form of treatment that improves patient well-being and further offers a new avenue for reducing the cost of care for subjects afflicted with edema. Further encompassed in the present disclosure is the treatment of nephrogenic diabetes insipidus (NDI) by administering pharmaceutically active relaxin to afflicted individuals.

DEFINITIONS

The term "modulating" refers to the capacity to regulate or adjust the activity and/or presence and/or effect of a biological entity including, but not limited to, a gene and a protein.

The term "tissue" refers to a collection of cells from the same origin. For example, a mammalian tissue is a collection of cells from a mammalian species. The cells that make up the tissue are not necessarily identical but together they carry out a specific function. The term "edema" means an accumulation of fluid in a tissue and/or organ of a mammalian body. The term "administering" refers to giving or applying to a subject a pharmaceutical remedy or formulation via a specific route, including but not limited to, intravenously, subcutaneously, intramuscularly, sublingually, intranasally, intracerebrally, intracerebroventricularly, topically, intravitrealy and via inhalation. The term "effective" as in "effective to reduce fluid accumulation associated with edema" refers to the amount of pharmaceutically active relaxin that will result in a measurable desired medical or clinical benefit to a patient, as compared to the patient's baseline status or to the status of an untreated or placebo-treated subject (e.g., not treated with relaxin).

The term "relaxin" refers to a peptide hormone which is well known in the art. The term "relaxin", as used herein, encompasses human relaxin, including intact full length human relaxin or a portion of the relaxin molecule that retains biological activity. The term "relaxin" encompasses human H1 preprorelaxin, prorelaxin, and relaxin; H2 preprorelaxin, prorelaxin, and relaxin; and H3 preprorelaxin, prorelaxin, and relaxin. The term "relaxin" further includes biologically active (also referred to herein as "pharmaceutically active") relaxin from recombinant, synthetic or native sources as well as relaxin variants, such as amino acid sequence variants. As such, the term contemplates synthetic human relaxin and recombinant human relaxin, including synthetic H1, H2 and H3 human relaxin and recombinant H1, H2 and H3 human relaxin. The term further encompasses active agents with relaxin-like activity, such as relaxin agonists and/or relaxin analogs and portions thereof that retain biological activity, including all agents that competitively displace bound relaxin from a relaxin receptor (e.g., RXFP1 receptor, RXFP2 receptor, RXFP3 receptor, RXFP4 receptor, previously known as LGR7, LGR8, GPCR135, GPCR142, respectively). Thus, a pharmaceutically effective relaxin or relaxin agonist is any agent with relaxin-like activity that is capable of binding to a relaxin receptor to elicit a relaxin-like response. In addition, a pharmaceutically effective relaxin or relaxin agonist is any agent with relaxin-like activity that is capable of up- and/or down-regulating and/or modifying expression of an aquaporin molecule (AQP), thereby modulating and/or changing the permeability of biological membranes to water which in turn can alter the fluid content of body tissues and/or organs. In addition, the nucleic acid sequence of human relaxin as used herein must not be 100% identical to nucleic acid sequence of human relaxin (e.g., H1, H2 and/or H3) but may be at least about 40%, 50%, 60%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99% identical to the nucleic acid sequence of human relaxin. Relaxin, as used herein, can be made by any method known to those skilled in the art. Examples of such methods are illustrated, for example, in U.S. Pat. No. 5,759,807 as well as in Bullesbach et al. (1991) *The Journal of Biological Chemistry* 266:10754-10761. Examples of relaxin molecules and analogs are illustrated, for example, in U.S. Pat. No. 5,166,191. Naturally occurring biologically active relaxin may be derived from human, murine (i.e., rat or mouse), porcine, or other mammalian sources. Also encompassed is relaxin modified to increase in vivo half life, e.g., PEGylated relaxin (i.e., relaxin conjugated to a polyethylene glycol), modifications of amino acids in relaxin that are subject to cleavage by degrading enzymes, and the like. The term also encompasses relaxin comprising A and B chains having N- and/or C-terminal truncations. In general, in H2 relaxin, the A chain can be varied from A(1-24) to A(10-24) and B chain from B(1-33) to B(10-22); and in H1 relaxin, the A chain can be varied from A(1-24) to A(10-24) and B chain from B(1-32) to B(10-22). Also included within the scope of the term "relaxin" are other insertions, substitutions, or deletions of one or more amino acid residues, glycosylation variants, unglycosylated relaxin, organic and inorganic salts, covalently modified derivatives of relaxin, preprorelaxin, and prorelaxin. Also encompassed in the term is a relaxin analog having an amino acid sequence which differs from a wild-type (e.g., naturally-occurring) sequence, including, but not limited to, relaxin analogs disclosed in U.S. Pat. No. 5,811,395. Possible modifications to relaxin amino acid residues include the acetylation, formylation or similar protection of free amino groups, including the N-terminal, amidation of C-terminal groups, or the formation of esters of hydroxyl or carboxylic groups, e.g., modification of the tryptophan (Trp) residue at B2 by addition of a formyl group. The formyl group is a typical example of a readily-removable protecting group. Other possible modifications include replacement of one or more of the natural amino-acids in the B and/or A chains with a different amino acid (including the D-form of a natural amino-acid), including, but not limited to, replacement of the Met moiety at B24 with norleucine (Nle), valine (Val), alanine (Ala), glycine (Gly), serine (Ser), or homoserine (HomoSer). Other possible modifications include the deletion of a natural amino acid from the chain or the addition of one or more extra amino acids to the chain. Additional modifications include amino acid substitutions at the B/C and C/A junctions of prorelaxin, which modifications facilitate cleavage of the C chain from prorelaxin; and variant relaxin comprising a non-naturally occurring C peptide, e.g., as described in U.S. Pat. No. 5,759,807. Also encompassed by the term "relaxin" are fusion polypeptides comprising relaxin and a heterologous polypeptide. A heterologous polypeptide (e.g., a non-relaxin polypeptide) fusion partner may be C-terminal or N-terminal to the relaxin portion of the fusion protein. Heterologous polypeptides include immunologically detectable polypeptides (e.g., "epitope tags"); polypeptides capable of generating a detectable signal (e.g., green fluorescent protein, enzymes such as alkaline phosphatase, and others known in the art); therapeutic polypeptides, including, but not limited to, cytokines, chemokines, and growth factors. All such variations or alterations in the structure of the relaxin molecule resulting in variants are included within the scope of this disclosure so long as the functional (biological) activity of the relaxin is maintained. Preferably, any modification of relaxin amino acid sequence or structure is one that does not increase its immunogenicity in the individual being treated with the relaxin variant. Those variants of relaxin having the described functional activity can be readily identified using in vitro and in vivo assays known in the art.

Relaxin

Relaxin is a polypeptide hormone that is similar in size and shape to insulin. It is an endocrine and autocrine/paracrine hormone belonging to the insulin gene superfamily. The active form of the encoded protein consists of an A chain and a B chain, held together by disulphide bonds, two inter-chains and one intra-chain. Thus, the structure closely resembles insulin in the disposition of disulphide bonds. In humans, there are three known non-allelic relaxin genes, relaxin-1 (RLN-1 or H1), relaxin-2 (RLN-2 or H2) and relaxin-3 (RLN-3 or H3). H1 and H2 share high sequence homology.

There are two alternatively spliced transcript variants encoding different isoforms described for this gene. H1 and H2 are differentially expressed in reproductive organs (U.S. Pat. No. 5,023,321 and Garibay-Tupas et al. (2004) *Molecular and Cellular Endocrinology* 219:115-125), while H3 is found primarily in the brain. The evolution of the relaxin peptide family in its receptors is generally well known in the art (Wilkinson et al. (2005) *BMC Evolutionary Biology* 5:1-17; and Wilkinson & Bathgate (2007), Chapter 1, Relaxin and Related Peptides, Landes Bioscience and Springer Science+ Business Media). Relaxin, relaxin receptors, and relaxin agonists are further described in detail in Patent Application Publication No. 20100048475.

Aquaporin-Associated Physiology and Disorders

Not surprisingly, the aquaporins (AQPs) are implicated in many physiological processes. For example, in the kidney, AQP1 is abundant in both the apical and the basolateral membranes of the renal proximal tubules and in the capillary endothelium. As such, AQP1 contributes to the counter-current mechanism for urine concentration and exchange. In the salivary gland, AQP3 is found in basolateral membranes, where water is taken up from the interstitium, and AQP5 is found in the apical membrane, where water is released. A range of clinical disorders is linked to the loss or dysfunction of aquaporins, including abnormalities of kidney function, loss of vision, onset of brain edema and starvation. In addition, AQP1 is believed to be involved in angiogenesis, wound healing, organ regeneration and carcinogenesis (Kruse et al. (supra)).

AQP4, a glial cell membrane water channel, is linked to brain edema, which plays an important role in the morbidity of nervous system disorders such as head trauma, tumors, stroke, infection, and metabolic disorders. The current treatment options for brain edema are limited to hyperosmolar agents and surgical decompression, which are therapies that were introduced more than 70 years ago. Some studies have shown that mice that are deficient in AQP4 have better survival than wild-type mice in a model of brain edema caused by acute water intoxication. Herein, brain tissue water content and swelling of pericapillary astrocytic foot processes in AQP4-deficient mice can be reduced. The characteristic swelling of astrocytic foot processes is also found in brain tissue from head injured patients. In another model of brain edema, such as ischemic stroke produced by middle cerebral artery occlusion, AQP4-deficient mice have improved neurological outcome as well. The condition of cerebral edema is measured via the percentage of hemispheric enlargement at 24 hours, and is found to be decreased by 35% in AQP4-deficient mice. Such findings suggest a key role for AQP4 in modulating brain water transport, and further suggest that AQP4 inhibition may provide a new therapeutic option for reducing brain edema in a wide variety of cerebral disorders (Manley et al. (2000) *Nature Medicine* 6:159-163). However, in another study, direct activation of the astrocytic ETB receptor is suggested to decrease AQP4 expression resulting in reduced excretion of edema fluid and leading to an aggravation of vasogenic brain edema (Koyama et al. (2010) *Neuroscience Letters* 469:343-347). This study further suggests that cytotoxic edema may be improved by a decrease in AQP4 expression due to the prevention of water entry while vasogenic edema may be improved by an increase in AQP4 expression due to the increased efflux of edema fluid.

Expression of AQP1, AQP4 and AQP9 are being studied in brain during pregnancy. Here, real-time quantitative PCR is used in different brain region during pregnancy and the post-partum state to assess the expression of aqp1, aqp4 and aqp9. There are pathologic conditions during pregnancy, which involve cerebral edema formation including posterior reversible encephalopathy syndrome, eclampsia and pre-eclampsia. Eclampsia and pre-eclampsia are serious complications of pregnancy, in which neurologic symptoms arise. These symptoms develop because of vasogenic brain edema due to an acute elevation of blood pressure. Edema formation in eclampsia is primarily found in the posterior brain regions. Notably, a higher expression of AQP4 is observed in the posterior cerebrum vs. the anterior cerebrum in both late pregnant animals and postpartum animals, which are two states during which eclampsia usually develops (Wiegman et al. (2008) *Reproductive Sciences* 15:506-516).

AQP1 and AQP5 are linked to corneal swelling and edema. Corneas with edema-related diseases lose transparency resulting in significant vision loss. AQP1 and AQP5 are expressed in corneal endothelial and epithelial cells, respectively, and function to facilitate osmotically driven water transport. In order to test whether these aquaporins are involved in corneal fluid transport and transparency, transgenic mice were made. For example, corneal thickness, water permeability, and response to experimental swelling were compared in wild type mice and transgenic null mice lacking aqp1 and aqp5. It was found that the deletion of aqp5 in mice increases corneal thickness and reduces osmotic water permeability across the corneal epithelium. Furthermore, it was found that aqp1 deletion reduces corneal thickness and osmotic water permeability across the corneal endothelium and impairs the restoration of corneal transparency after experimental swelling. Hence, the inhibition of AQP5 or AQP1 by non-toxic blockers may alter corneal structure and water content. In addition, the up-regulation of AQP1 in corneal endothelium may be particularly useful in reducing corneal edema and improving transparency after injury (Thiagarajah et al. (2002) *The Journal of Biological Chemistry* 277: 19139-19144). Similarly, AQP1, AQP3 and AQP4 have been linked to Pseudophakic Bullous Keratopathy (PBK), Aphakic Bullous Keratopathy (ABK) and Fuch's Dystrophy. These disorders are corneal diseases that have endothelial cell dysfunction and chronic edema as major components of the pathophysiology. When these conditions are present, fluid accumulates within epithelial cells and corneal thickness can increase substantially causing loss of transparency and decreased vision. It was found that in PBK and ABK corneas have altered distribution in AQP1, AQP3 and AQP4 while in Fuch's Dystrophy corneas have AQP1 changes (Kennedy et al. (2004) *Journal of Histochemistry and Cytochemistry* 52:1341-1350).

Aquaporins are also implicated in clinical disorders of urinary dilution and concentration. AQP1, and particularly, AQP2, AQP3, and AQP4, along with urea and ion transporters, have permitted a better understanding of urinary dilution and concentration at the cellular and molecular levels. For example, AQP1 is constitutively expressed on both the apical and the basolateral membranes of the proximal tubule and descending limb of Henle's loop. aqp1 knockout mice suffer from a diminished maximal urinary osmolality. The same is true for humans who lack the aqp1 gene. AQP3 and AQP4 are located on the basolateral membrane of the principal cells in the collecting duct. AQP3 is regulated by arginine vasopressin (AVP). aqp3 knockout mice exhibit substantial polyuria secondary to vasopressin-resistant nephrogenic diabetes insipidus (NDI). AQP4 predominates on the basolateral membrane of the inner medulla and is not regulated by AVP. aqp4 knockout mice also exhibit NDI but one that is less severe than that observed in the aqp3 knockout mice. AQP3 and AQP4 constitute the exit channels for water movement across the basolateral membrane of the collecting duct, while AQP2 is the water channel for water reabsorption across the apical membrane of the principal cells of the collecting duct. In fact, AQP2 is found exclusively in the principal cells of the collecting tubule and collecting duct regulated by arginine vasopressin (AVP). However, some findings suggest an AQP2 regulation by hyperosmolality that is independent of AVP. Among many other disorders, a water imbalance can lead to either clinically relevant hyponatremia or hypernatremia. Hyponatremia is more common and is the most frequent fluid and electrolyte disturbance in hospitalized patients, i.e., with the prevalence of hyponatremia in hospitalized patients being as high as 15 to 30% (Schrier (2006) *Journal of the American Society of Nephrology* 17:1820-1832).

Relaxin Modulates Aquaporins to Affect Reproductive Physiology

Figure 3:
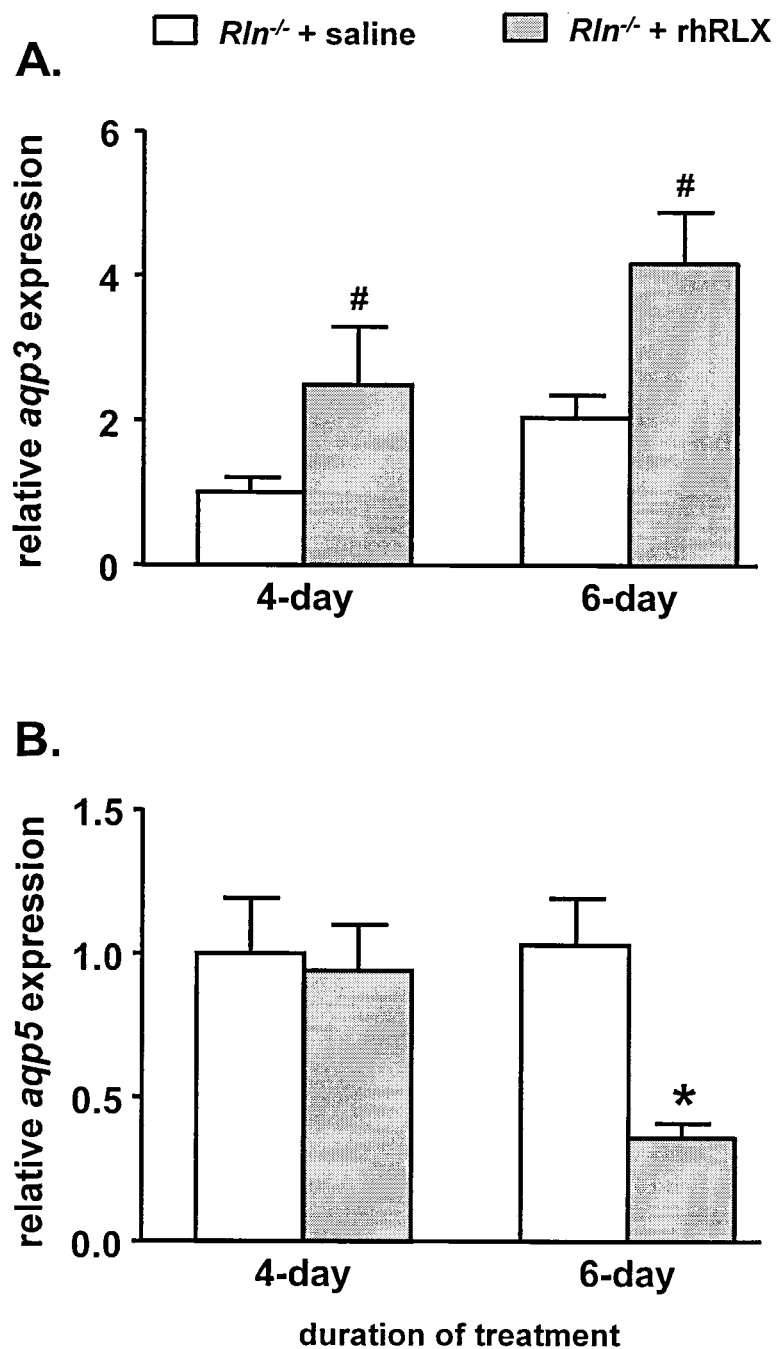
FIGS. 3A-B. Figure A shows that relaxin treatment increases aqp3 gene expression in the cervic of pregnant Rln−/−mice. Figure B shows that relaxin treatment decreases aqp5 gene expression in the cervix of pregnant Rln−/− mice.
Figure 4:
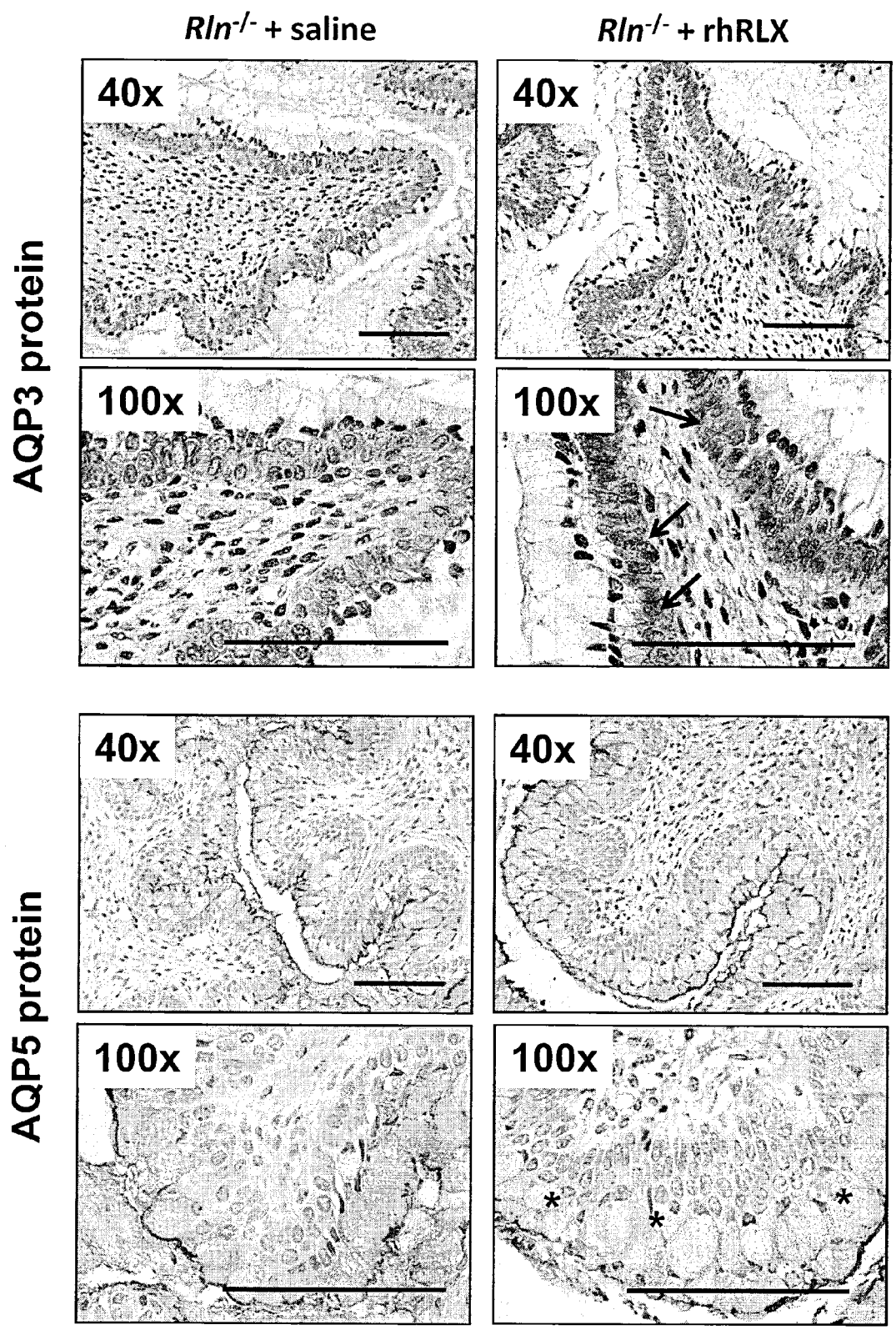
FIG. 4 shows that relaxin treatment increases AQP3 protein expression (arrows) and decreases AQP5 protein expression (asterisks) in the basal epithelial cells of the cervix of pregnant Rln−/− mice.

In late pregnancy, the extracellular matrix (ECM) of the cervix changes extensively during cervical ripening to allow the fetus to pass through the birth canal during labor. Cervical ripening is brought about by a complex series of events leading to collagen degradation and dispersal. The ovarian peptide relaxin is one factor involved in these processes, but current theories on the mechanisms of relaxin action have left many questions to answer. The applicants tested the new hypothesis that relaxin increases cervical water content and collagen fiber dispersal by regulating aquaporins (AQPs) (see Example 1). They showed that aqp3 gene expression was significantly reduced in the cervix of relaxin knockout (Rln−/−) mice at the end of pregnancy (FIG. 1). AQP3 protein was localized predominantly to the basal epithelial cells in the mouse cervix and there was a reduction in immunoreactive-AQP3 in this region in Rln−/− mice (FIG. 1). In a second study, pregnant Rln−/− mice were treated with relaxin, which resulted in a significant increase in cervical aqp3 and decrease in aqp5 gene expression compared with placebo controls (FIG. 3). Pregnant Rln−/− mice treated with relaxin had higher immunoreactive AQP3 in the basolateral epithelium and lower immunoreactive AQP5 in the basal cell of the epithelium compared to placebo controls (FIG. 4). In addition, relaxin treatment significantly increased cervical wet weight and collagen dispersal within the stromal ECM. These findings showed that relaxin modulates aquaporin gene and protein expression, and may modulate water balance in reproductive tissues.

AQP5 is likely regulated by a cAMP. This is believed to occur through protein kinase A (PKA) activation since inhibition of PKA blocks cAMP-mediated AQP5 translocation in lung epithelial MLE-12 (Sidhaye et al. (2005) *The Journal of Biological Chemistry* 280:3590-3596). As noted above, relaxin treatment of pregnant Rln−/− mice decreased AQP5 expression compared to saline-treated controls. Herein, ELISA data showed that relaxin concentrations were lower on the 6th day of infusion but the lower relaxin concentration did not reduce the inhibitory effects of relaxin on AQP5 expression. The applicants postulate that relaxin may regulate AQP5 expression or translocation through a cAMP pathway, which involves activation of PKA. Relaxin also activates cAMP in a biphasic manner via phosphoinositide 3-kinase (PI3K) activation, which is required for the second wave (Dessauer & Nguyuen (2005) *Annals of the New York Academy of Sciences* 1041:272-279). In the cervix, the functional importance of AQP5 in early pregnancy is to allow influx of water into the stroma and also an increase in mucosal secretion in the epithelial cells (Anderson et al. (2006) *Endocrinology* 147:130-140). The inventors contemplate that the decrease in AQP5 expression of late pregnant Rln+/+ mice suggests an inhibitory effect by naturally present relaxin.

Another possible mechanism for AQP5 involves an inflammatory agent. Cervical ripening has been suggested to be an inflammatory response due to high levels of inflammatory agents found in the pregnant cervix. The precise mediation and inter-relationships of inflammatory agents such as cytokines, notably IL-8, or platelet activating factor (PAF), monocyte chemotactic protein-1 (MCP-1) and macrophages in the cervix remains to be determined, but highest levels of inflammatory factors coincide with the active phase of cervical ripening. In terms of AQP5 regulation, a possible pathway is the activation of the canonical NF-kB pathway through TNF-alpha, an inflammatory factor, which binds to TNFR1 to inhibit and/or down-regulate AQP5 mRNA (2-fold) and protein (10-fold) (Towne et al. (2001) *The Journal of Biological Chemistry* 276:18657-18664). AQP5 is also up-regulated through an independent ERK pathway but only during hyperosmotic conditions in MLE-15 cells (Hoffert et al. (2000) *The Journal of Biological Chemistry* 275:9070-9077). Although NF-kB activates multiple signaling pathways such as ERK and MEK, the primary effect on AQP5 regulation is directly from the NF-kB transcripts. The link here is that recent investigations reported that in human THP-1 cells, relaxin increases two NF-kB subunits, p50 and p65 (transcriptional activators) and decreases the IkB-alpha which inhibits NF-kB translocation into the nucleus (Ho et al. (2007) *Journal of Leukocyte Biology* 81:1303-1310). However, this study was carried out to show MMP-9 induction by relaxin via the NF-kB pathway and is, thus, but one possible mechanism.

Relaxin Modulates Aquaporins to Affect Fluid Homeostasis

Most research on the peptide hormone relaxin focuses on mammalian reproduction because the hormone is secreted from the ovary in high concentrations during pregnancy. Its classic roles are associated with tissue remodeling processes that occur in the extracellular matrix of the cervix and vagina before the start of labor in animals. However, it has now become apparent that relaxin plays an important role in the kidney.

Figure 6:
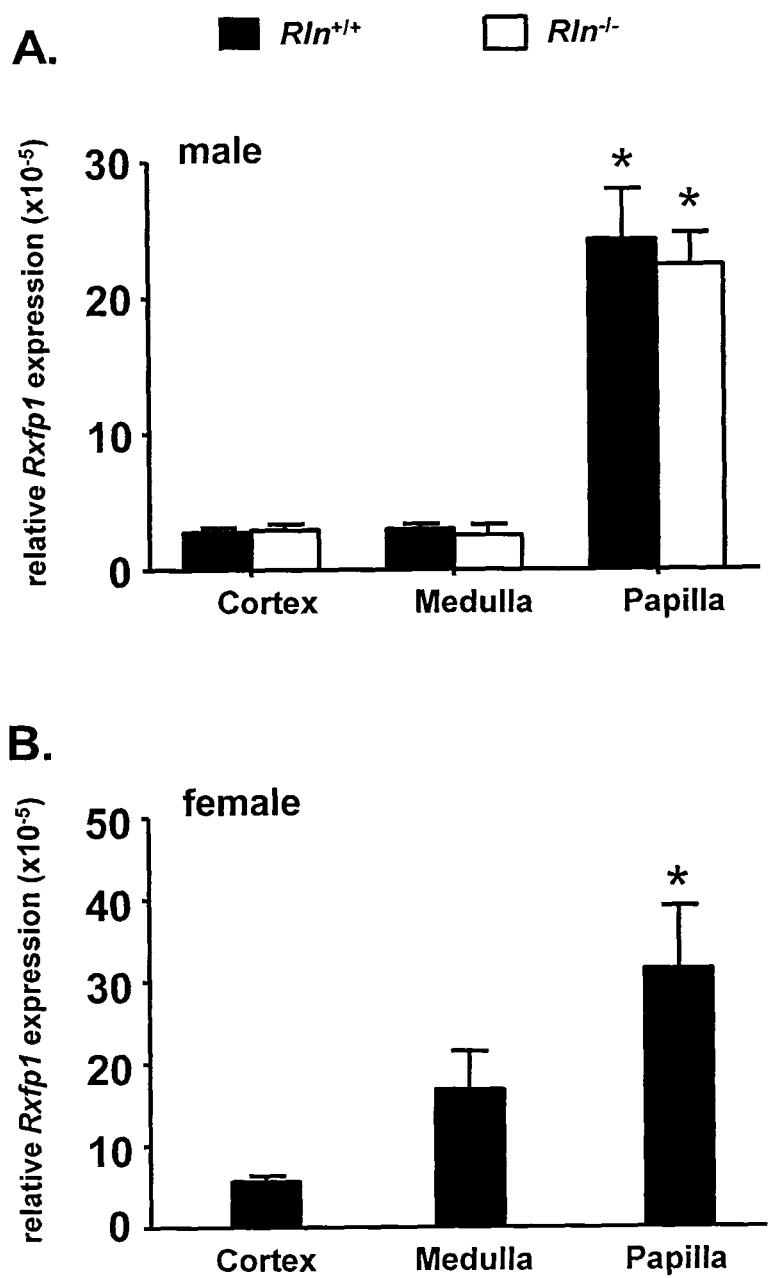
FIG. 6 shows expression of the Rxfp1 relaxin receptor by quantitative PCR in the kidney of male mice (FIG. 6A) and female mice (FIG. 6B).
Figure 7:
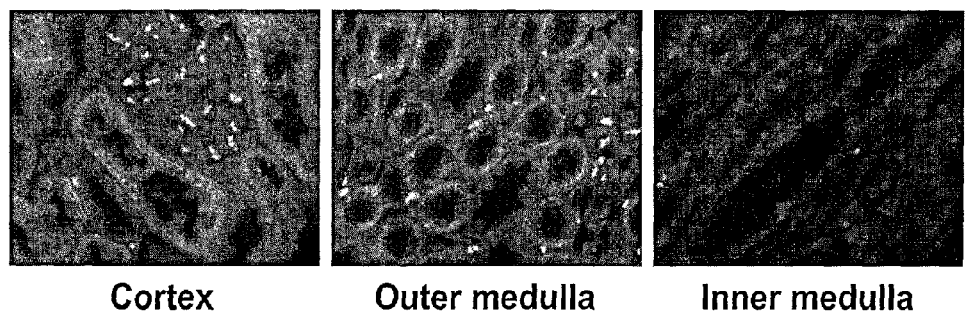
FIGS. 7A-D show expression of the Rxfp1 relaxin receptor in the kidney of male and female rats.
Figure 7:
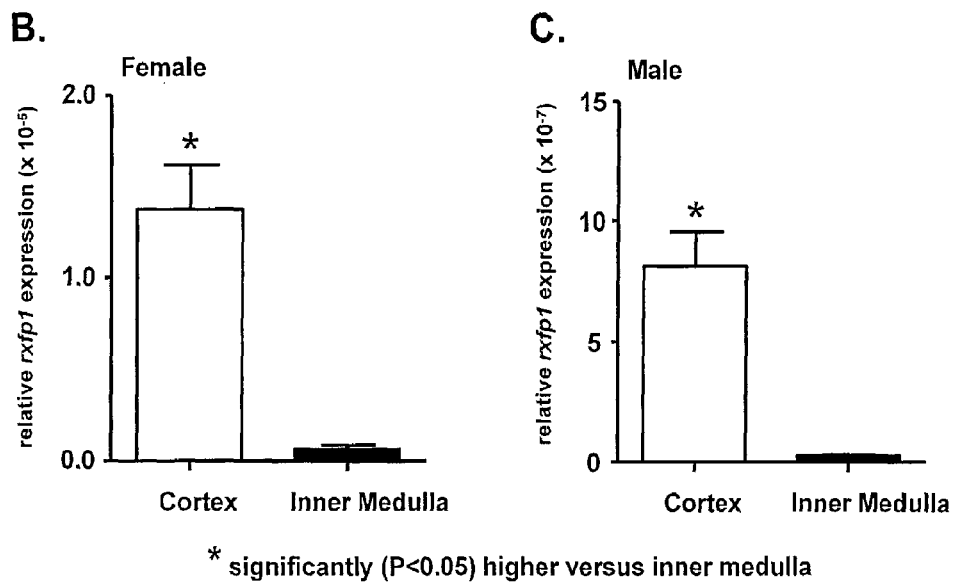

It is known that certain desert animals deal with the problem of limited water availability through a variety of morphological, behavioral, and physiological adaptations. In particular, they are able to concentrate their urine to prevent large amounts of water being lost when metabolic waste is excreted. This is thought to be the single-most important water conserving mechanism available to terrestrial vertebrates, especially in arid environments. Water conservation occurs in the collecting duct of the nephron of the kidney. If plasma osmolality (i.e., a measure of solute concentration as defined as the number of osmoles (Osm) of solute per liter (L) of solution) increases, these ducts become highly permeable to water and water moves out of the nephron into the surrounding medulla. One of the main urine-concentrating mechanisms associated with water reabsorption relies on the hormone vasopressin and its interactions with specific water channel molecules (i.e., the aquaporins), specifically AQP2 in the collecting ducts that extend into the renal papilla. However, little is know about the specific function of the renal papilla. Interestingly, spiny mice tolerate large increase in plasma osmolality after salt ingestion without having to drink lots of water, whereas laboratory mice have to drink. For example, spinifex hopping mice respond to water deprivation by decreasing urine volume and increasing urine osmolality very rapidly. The same does not occur in the laboratory mouse. Hence, the inventors set out to investigate the urine concentrating mechanism in laboratory mice and rats in order to correlate these findings to other mammals, including humans. This proved to be challenging since urine concentrating mechanism do not rely on increased vasopressin or renin-angiotensin. Herein, the inventors contemplate a novel function for the peptide hormone relaxin and its receptor, RXFP1, in the production of concentrated urine in the kidney, especially in response to water deprivation and increased salinity. The inventors contemplate that relaxin is a key regulatory factor in the production of concentrated urine in the kidney, and that relaxin acts directly on the inner medulla collecting duct cells to stimulate intracellular cAMP and mediate AQP2 trafficking to the apical membrane (see Example 2). The inventors found a high expression of RXFP1 in the laboratory mouse papilla (see FIG. 6), i.e., a specific region of the kidney that expresses AQP2 and AQP4 (see FIGS. 8 and 10). The inventors also found expression of RXFP1 in the renal tubules in both the cortex and medulla region of the laboratory rat kidney (FIG. 7). These findings in different species provide evidence of receptors for relaxin in the regions of the kidney that express AQP2 and AQP4, which are responsible for water permeability. In addition, relaxin could act independently of vasopressin and have a direct osmoregulatory effect on the kidney itself (see Example 2). The inventors found that relaxin treatment in mice and rats increases the expression of AQP2 and AQP4 in the kidney (see FIGS. 8, 10 and 11). This establishes the first link between relaxin and the aquaporins. Relaxin treatment in rats is also known to stimulate vasopressin release by increasing nerve activity in the brain (McKinley et al. (2004) *Journal of Neuroendocrinology* 16:340-347). Based on these findings, the inventors propose that water-conserving mechanisms in the kidney rely on a direct regulatory action of relaxin with the aquaporins or an indirect regulatory action on AQPs involving vasopressin release from the brain.

Treatment of Edema with Relaxin

Edema is a form of swelling that is caused when fluid is trapped in the tissues. It happens most often in the lower limbs, i.e., the feet, ankles, and legs but it can also occur in other parts of the body, such as the face and hands. Edema can occur from sitting or standing in one place for too long because water gets pulled down into legs and feet via gravity. Edema can also be the result of a weakening in the valves of the veins in the legs (i.e., venous insufficiency). This condition makes it difficult for the veins to push blood back up to the heart, and, thus, it leads to varicose veins and a build up of fluid in the legs. Specific diseases or conditions (e.g., congestive heart failure, lung disease, liver disease, kidney disease, thyroid disease, traumatic head injury) can cause edema or make it more pronounced. Pregnancy can cause edema in the legs as the uterus puts pressure on the blood vessels in the lower trunk of the body. In addition, preeclampsia and eclampsia, conditions that are associated with pregnacy can lead to edema. Preeclampsia causes changes within the blood vessels that cause them to "leak" into the tissues. The leaking causes swelling of the tissues, which results in edema. If the preeclampsia becomes more severe, swelling can occur in the liver, potentially leading to rupture of the liver with hemorrhage. Sometimes swelling can also occur in the brain, leading to seizures, which is known as eclampsia.

Cerebral edema is a dangerous condition that can lead to death if untreated. It is the result of excess accumulation of water in the intracellular and/or extracellular spaces of the brain. There are different forms of cerebral edema, including vasogenic cerebral edema which is further divided into hydrostatic cerebral edema which occurs in acute and malignant hypertension; cerebral edema caused by brain cancer; and high altitude cerebral edema (HACE). In addition to vasogenic cerebral edema there is cytotoxic cerebral edema (i.e., due to a disruption in cellular metabolism resulting in inadequate functioning of the sodium and potassium pump in the glial cell membrane which leads to cellular retention of sodium and water and swollen astrocytes in gray and white matter); osmotic cerebral edema (i.e., cerebral-spinal fluid (CSF) and extracellular fluid (ECF) osmolality of the brain is disrupted, thereby creating an abnormal pressure gradient so that water flows into the brain); and interstitial cerebral edema (as in obstructive hydrocephalus where the edema is due to rupture of the CSF-brain barrier resulting in trans-ependymal flow of CSF which permits CSF to penetrate brain and spread in the extracellular space of white matter).

Vasogenic edema is caused by a breakdown of the blood brain barrier. This allows intravascular proteins and fluid that are normally sequestered to penetrate into the cerebral parenchymal extracellular space. Once plasma components cross the blood brain barrier, the edema spreads and often quite rapidly. When the water enters white matter it moves extracellularly along fiber tracts and this can also affect the gray matter. This type of edema is found in response to head trauma, tumors, focal inflammation, late stages of cerebral ischemia and hypertensive encephalopathy. For example, within the United States alone, there are about two million emergency room visits for head injury, about 475,000 admissions for head trauma, about 52,000 deaths, and approximately 80,000 cases of severe long-term disability on a yearly basis. Yet there is no FDA approved drug for the treatment of severe head injury and resulting edema. Patients who present with traumatic head injury are often severely impaired and suffer from loss of consciousness, memory loss and focal neurological deficits that may or may not be transient.

Cerebral edema is believed to involve AQP1, AQP4 and AQP9. Particularly, AQP4, the most abundant aquaporin within the brain, appears to play a role in brain water physiology, brain edema and hydrocephalus (Brian et al. (2010) *Cerebrospinal Fluid Research* 7:15). In experimentally induced cerebral edema in rat models (e.g., via epison toxin treatment) AQP4 expression increases, which is consistent with previous findings (see Manley et al. (supra)). However, in another experimental model, direct activation of the astrocytic endothelin B (ETB) receptor is suggested to decrease AQP4 expression resulting in reduced excretion of edema fluid and leading to an aggravation of vasogenic brain edema (Koyama et al. (2010) *Neuroscience Letters* 469:343-347). Interestingly, this study further suggests that cytotoxic edema may be improved by a decrease in AQP4 expression due to the prevention of water entry while vasogenic edema may be improved by an increase in AQP4 expression due to the increased efflux of edema fluid. The inventors contemplate that relaxin treatment may decrease AQP4 expression in cytotoxic edema, which is consistent with relaxin being effective as an ETB receptor agonist and endothelin-1 antagonist (Dschietzig et al. (2003) *Circ Res.* 92:32-40). Relaxin may further increase AQP4 expression in vasogenic edema, which may occur via a second mechanism. Notably, the inventors have shown an increase in AQP4 expression in kidney tissue after treatment with relaxin (in addition to an increase in AQP2). Hence, a similar effect with respect to AQP4 may occur in cerebral tissue in vasogenic edema, which is consistent with AQP4 as a potential novel drug target (see Manley et al. and Koyama et al. (supra)).

Ocular edema is believed to involve AQP1, AQP3, AQP4 and AQP5. Ocular edema related to pseudophakic/aphakic bullous keratopathy (PBK/ABK) corneas and Fuchs' dystrophy corneas showed an increased expression of AQP3 and AQP4 in the diseased corneas which might contribute to swelling. The inventors contemplate that treating ocular edema with relaxin may cause a modulation of AQP3 and/or AQP4 in the cornea of a patient.

Pulmonary edema is believed to involve AQP1, AQP3, AQP4 and AQP5. In experimentally induced pulmonary edema in rat and mouse models AQP1, AQP4 and AQP5 expression decreases and AQP3 expression increases. For example, treatment with thiourea causes a very rapid decrease in expression of these aquaporins while hyperoxia treatment causes a decrease over 72 hours. The inventors contemplate that treating pulmonary edema with relaxin may be able to modulate AQP1, AQP3, AQP4 and/or AQP5. One possible scenario is an increase in AQP1, AQP4 and/or AQP5 expression and a decrease in AQP3 expression in the lung of a patient as a result of relaxin treatment.

It is contemplated that relaxin ameliorates systemic edema through a mechanism that regulates and/or modulates the water channels (i.e., the aquaporins) as described in detail in this disclosure. However, at least one of two additional mechanisms could contribute at least partially to a reduction in edema. Thus, the second mechanism that may also play a part is the regulation of ion transport and osmotic gradients, e.g., in pulmonary edema, relaxin might increase the ion transport, and hence, the osmotic gradient across the alveolar epithelial cells, thereby facilitating fluid clearance from the lung airspaces (Zemans et al. (2004) *Critical Care* 8:469-477). The third mechanism that may be involved is the regulation of hemodynamics, e.g., insofar as avid renal retention of sodium is a culprit underlying all forms of systemic edema, by improving renal hemodynamics and/or GFR, relaxin may facilitate renal sodium excretion, thereby improving systemic edema. In addition, relaxin may be natriuretic at least in the short term, which would facilitate renal sodium excretion in the setting of systemic edema (Jeyabalan & Conrad (2010) *Renal Physiology and Pathophysiology in Pregnancy. In: Renal and Electrolyte Disorders,* 4th Edition, R W Schrier, ed. Little Brown and Company).

In summary, the inventors have shown that relaxin is capable of modulating aquaporin expression in different tissues. Therefore, relaxin would be expected to be effective in the treatment of vasogenic edema because it increases aquaporin expression and promotes movement of water out of edematous tissues or organs, thereby reducing water accumulation and swelling. Alternatively, relaxin may decrease aquaporin expression and reduce further movement of water into tissues or organs, thereby preventing exacerbation of cytotoxic edema. In addition, relaxin may regulate solute transport between tissues and the blood, thereby affecting water movement in and out of tissues and reducing edema in tissues and organs. Furthermore, this may involve a hemodynamic action of relaxin on the vasculature in various organs to improve transport of water away from the affected organ.

The inventors have devised a method of treating edema in patients by administering relaxin. As such, patients are treated with a daily dose of pharmaceutically active relaxin (e.g., synthetic, recombinant, analog, agonist, etc.) in an amount in a range of about 1 to 1000 µg/kg of subject body weight per day. The term "about" when used in the context of a stated value, encompasses a range of up to 10% above or below the stated value (e.g., 90-110% of the stated value). For instance, an intravenous (IV) infusion rate of about 30 µg/kg/day, encompasses IV infusion rates of 27 µg/kg/day to 33 µg/kg/day. In one embodiment, the dosages of relaxin are 10, 30, 100 and 250 µg/kg/day. These dosages result in serum concentrations of relaxin of about 1, 3, 10, 30, 75 or 100 ng/ml. In one preferred embodiment, pharmaceutically effective relaxin or an agonist thereof is administered at about 30 µg/kg/day. In another preferred embodiment, pharmaceutically effective relaxin or an agonist thereof is administered at about 10 to about 250 µg/kg/day. In another embodiment, the administration of relaxin is continued as to maintain a serum concentration of relaxin of from about 0.5 to about 500 ng/ml, more preferably from about 0.5 to about 300 ng/ml, and most preferably from about 1 to about 10 ng/ml. Most preferably, the administration of relaxin is continued as to maintain a serum concentration of relaxin of 10 ng/ml or greater. These relaxin concentrations can ameliorate or reduce fluid accumulation associated with edema, including, but not limited to cerebral edema, ocular edema, pulmonary edema, ascites, hereditary angioedema, peripheral edema, and systemic edema.

Treatment of Nephrogenic Diabetes Insipidus (NDI) with Relaxin

Nephrogenic diabetes insipidus (NDI) is a condition that occurs when the kidney tubules do not respond to antidiuretic hormone (ADH), also called vasopressin. As a result, the urine concentration mechanism is impaired resulting in excessive dilute urine production of the afflicted subject. Besides the main symptom of excretion of large amounts of dilute urine (i.e., polyuria), the afflicted subject need to drink large amounts of water (i.e., polydipsia) to make up for the water lost in the urine. Additional complications include rapid dehydration, excessive thirst, irritability, lethargy, fever, vomiting, constipation or diarrhea, seizures, and failure to gain weight.

NDI is believed to be caused by a partial inactivating mutation or SNP in the V2 receptor. The inventors contemplate that relaxin improves NDI by a mechanism that increases cAMP in principle cells. Given that there is overlap in the cAMP pools for relaxin and AVP, then relaxin could enhance AQP2 and AQP3 insertion in the apical and basolateral membranes, respectively, as well as increase their expression in the setting of a partial inactivating mutation or SNP in the V2 receptor. However, at least one of two additional mechanisms could contribute at least partially to improving NDI. Thus, the second mechanism includes increasing cAMP in terminal collecting duct principal cells. cAMP signaling as above leads to insertion of UT-A1 and UT-A3 in the membrane facilitating urea deposition in the inner medulla which accounts for as much as 60% of the cortico-papillary osmotic gradient. The third mechanism includes increasing expression of the Na/K/2Cl cotransporter in the medullary thick ALH, which activity constitutes the "single effect" pivotal to formation of the C-P osmotic gradient, urinary concentration and dilution (Hebert & Andreoli (1984) *American Journal of Physiology* 246: F745-756).

The inventors have devised a method of treating NDI in patients by administering relaxin. Patients with NDI are treated via a subcutaneous pump supplying pharmaceutically active relaxin (e.g., synthetic, recombinant, analog, agonist, etc.) in an amount in a range of about 1 to 1000 µg/kg of subject body weight per day. In one embodiment, the dosages of relaxin are 10, 30, 100 and 250 µg/kg/day. These dosages result in serum concentrations of relaxin of about 1, 3, 10, 30, 75 or 100 ng/ml. In one preferred embodiment, pharmaceutically effective relaxin or an agonist thereof is administered at about 30 µg/kg/day. In another preferred embodiment, pharmaceutically effective relaxin or an agonist thereof is administered at about 10 to about 250 µg/kg/day. In another embodiment, the administration of relaxin is continued as to maintain a serum concentration of relaxin of from about 0.5 to about 500 ng/ml, more preferably from about 0.5 to about 300 ng/ml, and most preferably from about 1 to about 10 ng/ml. Most preferably, the administration of relaxin is continued as to maintain a serum concentration of relaxin of 10 ng/ml or greater. These relaxin concentrations can ameliorate or reduce the excessive dilute urine production and accompanying complication associated with NDI.

Relaxin Compositions and Formulations

Relaxin, relaxin agonists and/or relaxin analogs are formulated as pharmaceuticals to be used in the methods of the disclosure. Any composition or compound that can stimulate a biological response associated with the binding of biologically or pharmaceutically active relaxin (e.g., synthetic relaxin, recombinant relaxin) or a relaxin agonist (e.g., relaxin analog or relaxin-like modulator) to relaxin receptors can be used as a pharmaceutical in the disclosure. General details on techniques for formulation and administration are well described in the scientific literature (see Remington's Pharmaceutical Sciences, Maack Publishing Co, Easton Pa.). Pharmaceutical formulations containing pharmaceutically active relaxin can be prepared according to any method known in the art for the manufacture of pharmaceuticals. The formulations containing pharmaceutically active relaxin or relaxin agonists used in the methods of the disclosure can be formulated for administration in any conventionally acceptable way including, but not limited to, intravenously, subcutaneously, intramuscularly, sublingually, intranasally, intracerebrally, intracerebroventricularly, topically, orally, intravitrealy and via inhalation. Illustrative examples are set forth below. In one preferred embodiment, relaxin is administered intravenously or subcutaneously.

When relaxin is delivered by intravenous or subcutaneous injection (e.g., infusion, bolus, pump), the formulations containing pharmaceutically active relaxin or a pharmaceutically effective relaxin agonist can be in the form of a sterile injectable preparation, such as a sterile injectable aqueous or oleaginous suspension. This suspension can be formulated according to the known art using those suitable dispersing or wetting agents and suspending agents which have been mentioned above. The sterile injectable preparation can also be a sterile injectable solution or suspension in a nontoxic parenterally-acceptable diluent or solvent. Among the acceptable vehicles and solvents that can be employed are water and Ringer's solution, an isotonic sodium chloride. In addition, sterile fixed oils can conventionally be employed as a solvent or suspending medium. For this purpose any bland fixed oil can be employed including synthetic mono- or diglycerides. In addition, fatty acids such as oleic acid can likewise be used in the preparation of injectables.

Aqueous suspensions of the disclosure contain relaxin in admixture with excipients suitable for the manufacture of aqueous suspensions. Such excipients include a suspending agent, such as sodium carboxymethylcellulose, methylcellulose, hydroxypropylmethylcellulose, sodium alginate, polyvinylpyrrolidone, gum tragacanth and gum acacia, and dispersing or wetting agents such as a naturally occurring phosphatide (e.g., lecithin), a condensation product of an alkylene oxide with a fatty acid (e.g., polyoxyethylene stearate), a condensation product of ethylene oxide with a long chain aliphatic alcohol (e.g., heptadecaethylene oxycetanol), a condensation product of ethylene oxide with a partial ester derived from a fatty acid and a hexitol (e.g., polyoxyethylene sorbitol mono-oleate), or a condensation product of ethylene oxide with a partial ester derived from fatty acid and a hexitol anhydride (e.g., polyoxyethylene sorbitan monooleate). The aqueous suspension can also contain one or more preservatives such as ethyl or n-propyl p-hydroxybenzoate, one or more coloring agents, one or more flavoring agents and one or more sweetening agents, such as sucrose, aspartame or saccharin. Formulations can be adjusted for osmolarity.

Oil suspensions can be formulated by suspending relaxin in a vegetable oil, such as arachis oil, olive oil, sesame oil or coconut oil, or in a mineral oil such as liquid paraffin. The oil suspensions can contain a thickening agent, such as beeswax, hard paraffin or cetyl alcohol. Sweetening agents can be added to provide a palatable oral preparation. These formulations can be preserved by the addition of an antioxidant such as ascorbic acid.

Dispersible powders and granules of the disclosure suitable for preparation of an aqueous suspension by the addition of water can be formulated from relaxin in admixture with a dispersing, suspending and/or wetting agent, and one or more preservatives. Suitable dispersing or wetting agents and suspending agents are exemplified by those disclosed above. Additional excipients, for example sweetening, flavoring and coloring agents, can also be present.

The pharmaceutical formulations of the disclosure can also be in the form of oil-in-water emulsions. The oily phase can be a vegetable oil, such as olive oil or arachis oil, a mineral oil, such as liquid paraffin, or a mixture of these. Suitable emulsifying agents include naturally-occurring gums, such as gum acacia and gum tragacanth, naturally occurring phosphatides, such as soybean lecithin, esters or partial esters derived from fatty acids and hexitol anhydrides, such as sorbitan monooleate, and condensation products of these partial esters with ethylene oxide, such as polyoxyethylene sorbitan mono-oleate.

Administration and Dosing Regimen of Relaxin Formulations

The formulations containing pharmaceutically active relaxin or pharmaceutically effective relaxin agonist used in the methods of the disclosure can be administered in any conventionally acceptable way including, but not limited to, intravenously, subcutaneously, intramuscularly, sublingually, intranasally, intracerebrally, intracerebroventricularly, topically, orally, intravitrealy and via inhalation. Administration will vary with the pharmacokinetics and other properties of the drugs and the patients' condition of health. General guidelines are presented below.

The methods of the disclosure reduce fluid accumulation associated with edema. In addition, the methods of the disclosure reduce chronic excretion of dilute urine in patients with nephrogenic diabetes insipidus (NDI). The amount of relaxin alone or in combination with another agent or drug that is adequate to accomplish this is considered the therapeutically effective dose. The dosage schedule and amounts effective for this use, i.e., the "dosing regimen," will depend upon a variety of factors, including the stage of the disease or condition, the severity of the disease or condition, the severity of the adverse side effects, the general state of the patient's health, the patient's physical status, age and the like. In calculating the dosage regimen for a patient, the mode of administration is also taken into consideration. The dosage regimen must also take into consideration the pharmacokinetics, i.e., the rate of absorption, bioavailability, metabolism, clearance, and the like. Based on those principles, relaxin can be used to treat edema and/or NDI in individuals afflicted with these disorders.

The disclosure also provides the use of relaxin in the manufacture of a medicament for treating edema and/or NDI, wherein the medicament is specifically prepared for treating afflicted individuals. Further contemplated is the use of relaxin in the manufacture of a medicament for treating edema and/or NDI, wherein the patient has previously (e.g., a few hours before, one or more days before, etc.) been treated with a different drug. In one embodiment, the other drug is still active in vivo in the patient. In another embodiment, the other drug is no longer active in vivo in the patient.

The state of the art allows the clinician to determine the dosage regimen of relaxin for each individual patient. As an illustrative example, the guidelines provided below for relaxin can be used as guidance to determine the dosage regimen, i.e., dose schedule and dosage levels, of formulations containing pharmaceutically active relaxin administered when practicing the methods of the disclosure. As a general guideline, it is expected that the daily dose of pharmaceutically active H1, H2 and/or H3 human relaxin (e.g., synthetic, recombinant, analog, agonist, etc.) is typically in an amount in a range of about 1 to 1000 µg/kg of subject body weight per day. In one embodiment, the dosages of relaxin are 10, 30, 100 and 250 µg/kg/day. In another embodiment, these dosages result in serum concentrations of relaxin of about 1, 3, 10, 30, 75 or 100 ng/ml. In one preferred embodiment, pharmaceutically effective relaxin or an agonist thereof is administered at about 30 µg/kg/day. In another preferred embodiment, pharmaceutically effective relaxin or an agonist thereof is administered at about 10 to about 250 µg/kg/day. In another embodiment, the administration of relaxin is continued as to maintain a serum concentration of relaxin of from about 0.5 to about 500 ng/ml, more preferably from about 0.5 to about 300 ng/ml, and most preferably from about 1 to about 10 ng/ml. Most preferably, the administration of relaxin is continued as to maintain a serum concentration of relaxin of 10 ng/ml or greater. Thus, the methods of the present disclosure include administrations that result in these serum concentrations of relaxin. These relaxin concentrations can ameliorate or reduce fluid accumulation associated with edema, including, but not limited to cerebral edema, ocular edema, pulmonary edema, ascites, hereditary angioedema, peripheral edema, and systemic edema. Furthermore, these relaxin concentrations can ameliorate or reduce chronic excretion of dilute urine in NDI. Depending on the subject, the relaxin administration is maintained for as specific period of time or for as long as needed to achieve stability in the subject. For example, the duration of relaxin treatment is preferably kept at a range of about 4 hours to about 96 hours, more preferably 8 hours to about 72 hours, depending on the patient, and one or more optional repeat treatments as needed.

Single or multiple administrations of relaxin formulations may be administered depending on the dosage and frequency as required and tolerated by the patient who suffers from edema and/or NDI. The formulations should provide a sufficient quantity of relaxin to effectively ameliorate the condition. A typical pharmaceutical formulation for intravenous subcutaneous administration of relaxin would depend on the specific therapy. For example, relaxin may be administered to a patient through monotherapy (i.e., with no other concomitant medications) or in combination therapy with another medication. In one embodiment, relaxin is administered to a patient daily as monotherapy. In another embodiment, relaxin is administered to a patient daily as combination therapy with another drug. Notably, the dosages and frequencies of relaxin administered to a patient may vary depending on age, degree of illness, drug tolerance, and concomitant medications and conditions.

In some embodiments, relaxin is provided as a 1 mg/ml solution (3.5 ml in 5 ml glass vials). Placebo, which is identical to the diluent for relaxin, is provided in identical vials. Relaxin or placebo can be administered intravenously or subcutaneously to the patient in small volumes using a syringe pump in combination with normal saline in a piggyback configuration. Compatible tubing and a 3-way stopcock, which have been tested and qualified for use with relaxin are used to administer the relaxin formulation. Doses are administered on a weight basis and adjusted for each patient by adjusting the rate of relaxin drug delivered by, for example, the infusion pump.

EXAMPLES

The following specific examples are intended to illustrate the disclosure and should not be construed as limiting the scope of the claims.

Example 1

Relaxin Modulates Aquaporin-3 and Aquaporin-5 in the Cervix

Relaxin increases cervical water content and collagen fiber dispersal by regulating aquaporins (AQPs). Gene expression of aqp3 was significantly reduced in the cervix of relaxin knockout (Rln−/−) mice at the end of pregnancy (FIG. 1A). AQP3 protein was localized to the basolateral epithelium of the mouse cervix and there was a reduction in immunoreactive-AQP3 in this region in Rln−/− mice (FIG. 1B). In a second study, pregnant Rln−/− mice were treated with relaxin. This resulted in a significant increase in cervical aqp3 and decrease in aqp5 gene expression compared with placebo controls (FIG. 3). Pregnant Rln−/− mice treated with relaxin had higher immunoreactive AQP3 in the basolateral epithelium and lower immunoreactive AQP5 in the apical layers of the epithelium compared to placebo controls (FIG. 4). In addition, relaxin treatment significantly increased cervical wet weight and collagen dispersal within the stromal ECM. These findings showed that relaxin modulates aquaporin gene and protein expression, and may modulate water balance in reproductive tissues.

TABLE 1

| GENE and PROTEIN EXPRESSION | RELAXIN TREATMENT | SALINE TREATMENT | FUNCTIONAL IMPORTANCE |
|---|---|---|---|
| aqp3 and AQP3 | higher | no effect | Allows water efflux from cervical epithelial cells into the stroma. |
| aqp5 and AQP5 | lower | no effect | Allows water influx from lumen into the cervical epithelial cells. |

More specifically, relaxin gene knockout mice have higher cervical collagen densities at the end of pregnancy but this is not due to decreased MMPs. Herein, the inventors propose an alternative mechanism of relaxin action involving recruitment of water into the cervical stroma to increase cervical hydration and cause collagen fiber dispersal. The study referred to above tested the hypothesis that relaxin regulates aquaporins (AQPs). In more detail, cervices were collected from relaxin wild type and relaxin knock-out mice on days 14.5, 16.5, 18.5 and 19 of their pregnancy (pc), and day 1 postpartum to compare aqp3 and aqp5 gene expression between the genotypes by quantitative PCR analysis and protein expression by immunohistochemistry. In the second study referred to above, relaxin knock-out mice were implanted with Alzet osmotic minipumps on day 12.5 pc to infuse either recombinant H2 human relaxin (0.05 µg/h; Corthera, Inc) or 0.9% saline. Cervices were collected after 4 or 6 days of infusion. Relaxin treatment caused a significant increase in cervical aqp3 and decrease in aqp5 gene expression compared with placebo controls. Additionally, relaxin treatment caused a 6-fold increase in cervix wet weight and a decrease in relaxin receptor RXFP1 expression. These new findings suggest that relaxin up-regulates AQP3 in the basolateral region of the epithelium to maintain water influx into the stroma from the lumen (FIG. 4). Relaxin may also down-regulate AQP5 to prevent water loss from the apical region to the lumen (FIG. 4). These data suggest that relaxin promotes cervical hydration by modulating AQPs. This may facilitate cervical ripening by causing collagen fibril dispersal in the ECM.

Example 2

Relaxin Modulates Aquaporin-2 and Aquaporin-4 in the Kidney

Relaxin-deficient mice report abnormally high plasma osmolality, which is a measure of the concentration of electrolytes, urea and other ions in the blood. High plasma osmolality in these animals suggests that urine concentrating mechanisms in the renal tubule might be impaired. However, when animals are treated with relaxin, the reverse occurs and plasma osmolality decreases. The inventors contemplate that relaxin alters the "thirst recognition" center in the brain to stimulate arginine vasopressin (AVP) release which then acts on its V2 receptors in the collecting ducts to increase water permeability via AQP2. The inventors found that the RXFP1 relaxin receptor is, in fact, expressed in the kidneys of mice and rats (FIG. 7). This expression of RXFP1 was observed in the regions of the kidney responsible for water permeability, i.e., the papilla in mice and the inner medulla in rats (FIG. 7). These data suggest that relaxin could act independently of AVP and have a direct osmoregulatory effect on the kidney itself. The other possibility is that relaxin acts in synergy with AVP to enhance its water-conserving capabilities.

TABLE 2

| GENE EXPRESSION | RELAXIN TREATMENT | SALINE TREATMENT | FUNCTIONAL IMPORTANCE |
| --- | --- | --- | --- |
| aqp2 | higher | no effect | Facilitates water movement from the renal tubule filtrate into collecting duct cells. |
| aqp4 | higher | no effect | Facilitates water movement from the collecting duct cells and into the blood to lower plasma osmolality. |

Figure 8:
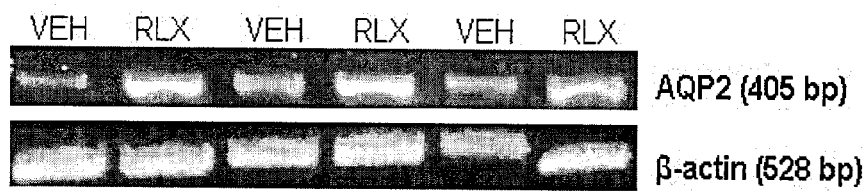
FIG. 8A shows an increase in aqp2 gene expression in the kidney of male Rln+/+ mice treated with relaxin compared with saline (VEH) controls. β-actin is the normalizing control.
FIG. 8B shows a moderate increase in aqp2 gene expression in the papilla of male Rln−/− mice treated with relaxin for five days.
FIG. 8C shows a small increase in aqp2 gene expression in the medulla of male rats treated with relaxin for five days.
Figure 8:
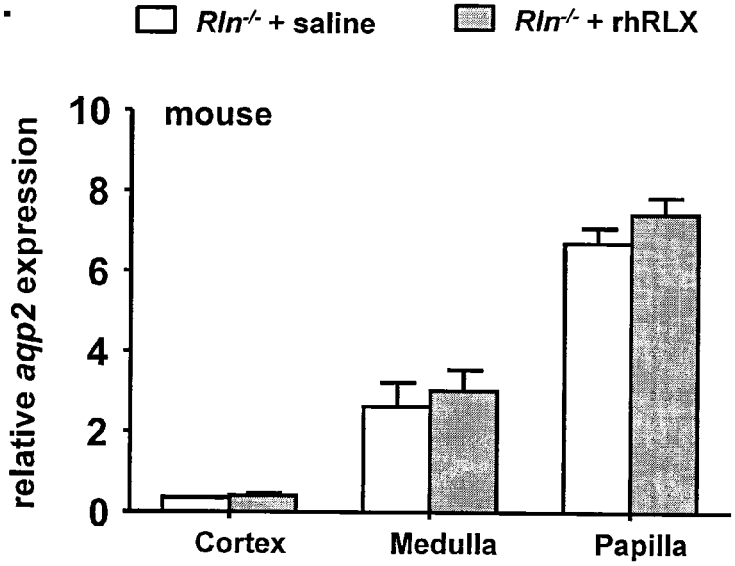
Figure 8:
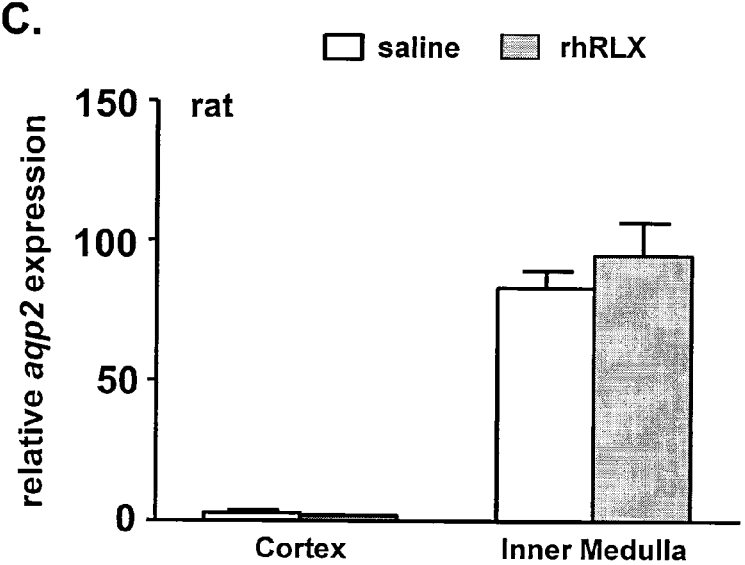

Relaxin treatment in mice and rats increased the expression of AQP2 in the kidney (FIG. 8). FIG. 8A depicts an increase in aqp2 gene expression in the kidney of male Rln+/+ mice treated with relaxin for 14 days compared with saline (VEH) controls, wherein β-actin is the normalizing control. FIG. 8B illustrates an increase in aqp2 gene expression in male Rln−/− mice treated with relaxin for five days. This finding provided a regulatory link between relaxin and aquaporins in the kidney. As a result, the inventors propose that water-conserving mechanisms in the kidney might rely on a direct action of relaxin to mediate aquaporins (AQPs) as well as an indirect action on AVP release from the brain.

Treatment with relaxin for five days in rats increased aqp2 gene expression in the medulla region (which includes the papilla) of the male rat kidney (FIG. 8C). This finding supports the speculation that relaxin may act within the kidney to increase AQP2 expression and regulate movement of water molecules from the renal tubule filtrate back into the blood in mammals.

Figure 9:
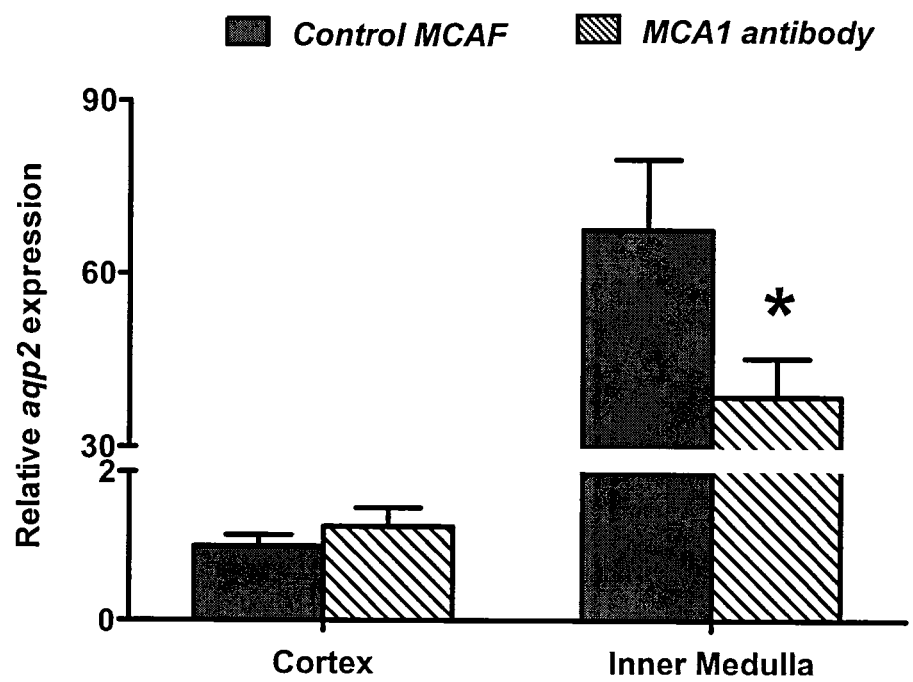
FIG. 9 shows that treatment with a monoclonal antibody against rat relaxin (MCA1) in late pregnant rats decreases aqp2 gene expression in the medulla region of the kidney.

Treatment with a monoclonal antibody against rat relaxin (MCA1) in pregnant rats reduced aqp2 gene expression in the medulla region of the kidney (FIG. 9). This finding supports the idea that endogenous relaxin plays a role in regulating aquaporins in the kidney. As a result, the inventors propose that pregnancy-related water-conserving mechanisms in the kidney might rely on a direct action of relaxin to mediate aquaporins.

Relaxin increases AQP4 in the kidney. The inventors first showed that aqp4 gene expression was significantly reduced in the papilla region of the kidney in Rln−/− mice as depicted in FIG. 10A. FIGS. 10B and 10C show that treatment with relaxin for either five days or 14 days in male Rln−/− mice increased aqp4 gene expression in the papilla. This finding supports the novel speculation that relaxin acts within the kidney to increase AQP4 expression and regulate movement of water molecules from the renal tubule filtrate back into the blood in mammals.

Figure 11:
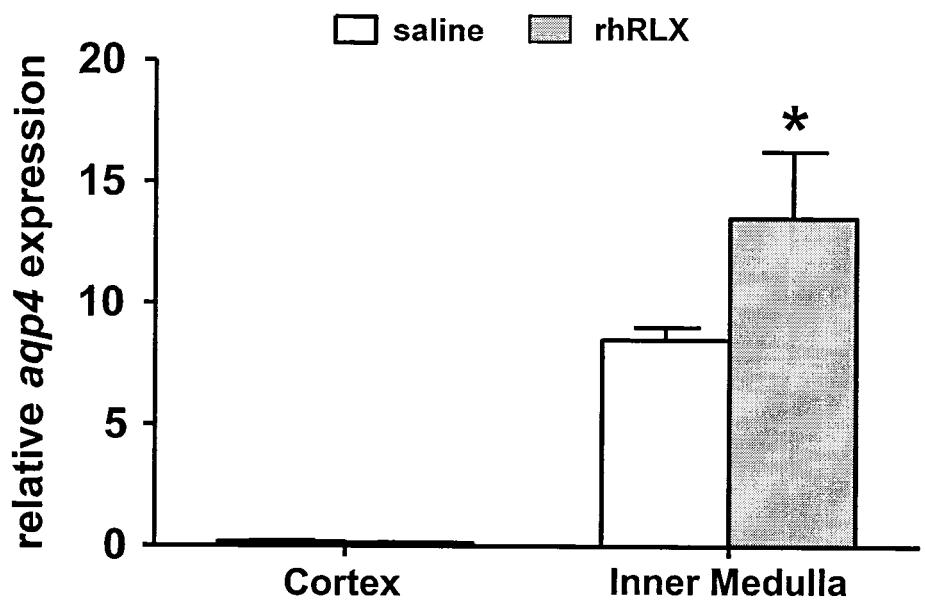
FIG. 11 shows an increase in aqp4 gene expression in the medulla of male rats treated with relaxin for five days.

Treatment with relaxin for five days in male rats increased aqp4 gene expression in the medulla region (which includes the papilla) of kidney (FIG. 11). This finding supports the novel idea that relaxin acts within the kidney to increase AQP4 expression in different mammals.

Example 3

Relaxin's Action on Collecting Duct Cells in the Kidney

Water-conserving mechanisms in the kidney may rely on a relaxin-mediated interaction with aquaporins (AQPs) as well as AVP. The AVP-deficient Brattleboro rat model can be used to evaluate the contribution of relaxin versus AVP in regulating AQP2 function in the renal collecting duct.

In this model, body mass, water and food consumption, feces and urine output are recorded daily. Urine samples are analyzed for electrolytes and urea by spectrophotometry (Synchron CX5CE Delta; Beckman Coulter). The osmolality is measured by freezing point depression (osmometer).

Nine pairs of kidneys are dissected into cortex and inner medulla for gene and protein analysis. Three pairs of kidneys are sectioned in half and fixed in PLP (Paraformaldehyde/Lysine/Periodate) for embedding in polyester wax for immunohistochemistry. Quantitative PCR (q-PCR) is used to measure gene expression and comparisons made between different kidney regions and the two species of mice. Protein expression is measured by Western blot analysis and immunohistochemistry. Plasma osmolality and AVP concentrations are also measured on the osmometer and by RIA, respectively.

Relaxin is predicted to increase water permeability in the collecting duct and enable these rats to concentrate their urine and therefore reduce excessive water loss. The inventors' discovery that relaxin treatment increased AQP2 expression in the kidney (supra) suggests that abnormally high plasma osmolality in relaxin-deficient animals could be related to defects in AQP2 expression or AQP2 vesicle translocation within the collecting duct.

Inner medulla collecting duct (IMCD) cells provide a model for demonstrating the role of relaxin in AVP-independent modulation of AQP2. IMCD cells are seeded on type IV collagen-coated Petri dishes with DMEM/F12 medium containing 10% BSA. Cells are grown to confluence for four days and treated on day five after seeding. For the measurement of cAMP levels and PKA activity in response to relaxin treatment, IMCD cells are incubated in medium containing human H2 relaxin (concentrations 0.1 pM-1 μM) for 45 minutes. The cells subjected to PKA inhibition are pre-incubated with 10 μM H-89 (a PKA inhibitor) for 60 minutes before H2 relaxin incubation. This concentration of H-89 is known to inhibit AQP2 phosphorylation in IMCD cells. After treatment, cells are snap frozen in lysis buffer. cAMP content and PKA activity is measured using commercially available kits (Cayman Chemical, USA). Standard molecular biology approaches can be used to measure Rxfp1 and aqp2 gene expression in IMCD cells. In order to assess the intracellular localization of AQP2, IMCD cells are fixed in 4% PFA after treatment and then incubated with an anti-AQP2 antibody and goat anti-rabbit IgG Alexa Fluor 488 secondary antibody to visualize AQP2 protein. Each experiment is repeated three times, with triplicates for each individual sample (n=9). The translocation of AQP2-containing vesicles to their site of action at the apical cell membrane can be detected by greater fluorescence in the periphery of the cell.

Example 4

Relaxin, Vasopressin and the Regulation of AQP2 in the Kidney

Figure 5:
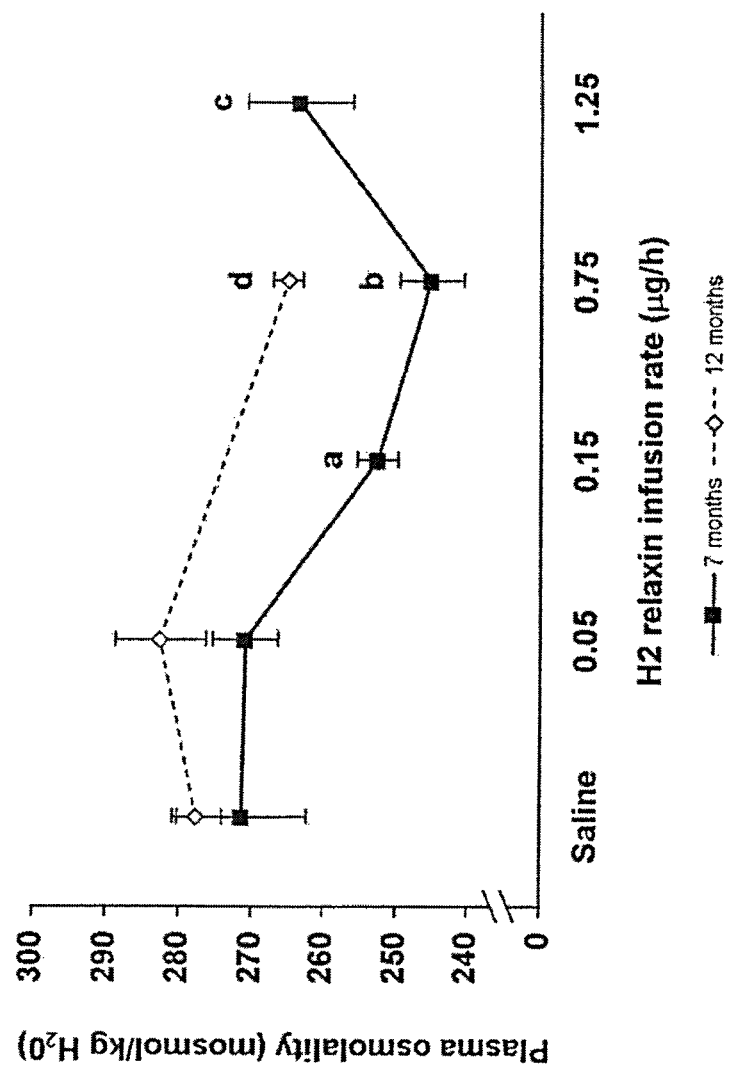
FIG. 5 shows the effects of relaxin treatment on plasma osmolality in male Rln−/− mice.

Relaxin may act on the kidney independently of vasopressin to regulate AQP2 and the production of concentrated urine. For methods and analysis see Example 2 (supra). Homozygous (di/di) Brattleboro rats have severe nephrogenic diabetes insipidus (NDI) caused by their inability to produce AVP. They excrete large quantities of dilute urine and drink copiously to replace this water loss. Because they have no AVP, there is a significant reduction in AQP2 in the collecting duct. Treatment of these animals with AVP enables them to concentrate their urine by increasing AQP2 translocation to the apical membrane. However, reports in the literature suggest that Brattleboro rats can concentrate their urine without AVP, especially after food deprivation. If relaxin can regulate AQP2 independently of AVP, then relaxin treatment in Brattleboro rats would be expected to increase AQP2 expression and may enable them to concentrate their urine. To test this hypothesis, the inventors use the experimental protocol outlined in FIG. 5, which shows the infusion period for relaxin and control (saline). Specifically, Brattleboro rats (♀ and ♂ aged 3-4 months) are habituated to rat-specific metabolic cages for two 24 hour periods with food and water. They are implanted with Alzet osmotic minipumps to deliver either 4 μg/h human H2 relaxin or saline for 72 hours. This infusion rate increases GFR and ERPF and decreases plasma osmolality in Long Evans rats. The controls for this study are age-matched Long-Evans rats. Body mass, water and food consumption, feces and urine output are measured at the time points shown in FIG. 5. Urine samples are analyzed for electrolytes and urea by spectrophotometry. Osmolality is measured by freezing point depression. A reduction in urine output and plasma osmolality in response to relaxin would indicate an improvement in the urine concentrating mechanisms of the kidney. Increased AQP2 expression would suggest that the action of relaxin on aquaporins is independent of vasopressin.

Example 5

Relaxin Reduces Cerebral Edema in Mice

Vasogenic brain edema occurs when there is a breakdown of tight junctions in the vascular endothelial cells of the blood-brain barrier. It leads to the entry of large amounts of plasma proteins and fluid into the extracellular spaces of nerve tissues and excess accumulation of water in the brain. AQP4-mediated transcellular water movement is crucial for fluid clearance in vasogenic brain edema (Papadopoulos et al. (2004) *FASEB Journal* 18: 1291-1293). Therefore, increases in brain AQP4 up-regulation could be a novel therapeutic option in vasogenic brain edema. Based on the increased AQP4 expression in relaxin-treated mammals in the kidney (see Example 2, supra), the inventors contemplate that relaxin treatment could also increase AQP4 expression in the brain. To test this hypothesis, male rats are implanted with Alzet osmotic minipumps and a brain infusion cannula to deliver 50-500 ng human H2 relaxin or saline for 24 or 72 hours. These doses of relaxin and infusion rate increase drinking behavior and plasma vasopressin in rats. Brain tissues are obtained from the cerebral cortex, brain stem and cerebellum and AQP4 gene and protein expression are analyzed by quantitative PCR, immunohistochemistry and Western blot analysis.

Figure 10:
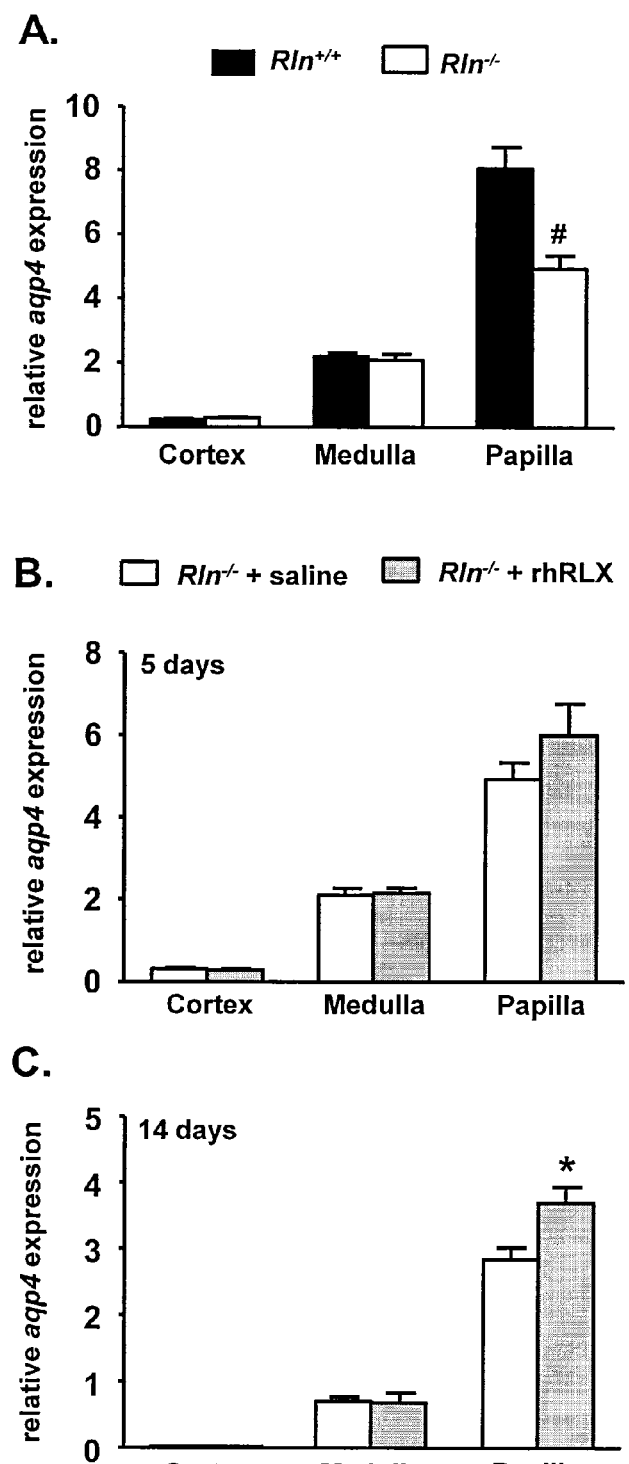
FIG. 10A shows the reduction in aqp4 gene expression in the kidney of male Rln−/− mice.
FIGS. 10B and 10C show that treatment with relaxin in male Rln−/− mice for either five or 14 days increases aqp4 gene expression in the papilla region of the kidney.
FIG. 10D shows an increase in aqp4 gene expression in the medulla of male rats treated with relaxin for five days.

Relaxin treatment in mice and rats increased the expression of AQP4 in the medulla region (which includes the papilla) of kidney (FIGS. 10 and 11). Herein, the inventors propose that relaxin acts within the brain to increase AQP4 expression and thereby reduce cerebral edema. In mice lacking AQP4 (Aqp4-/-), brain swelling is reduced following water intoxication and focal cerebral ischemia compared with wild-type mice (Manley et al. (2000) *Nature Medicine* 6:159-163). If relaxin up-regulates AQP4 in a manner similar to that shown in the kidney, the inventors predict that relaxin treatment in animal models of vasogenic edema would increase AQP4 expression in the brain and accelerate the elimination of edema fluid from the brain parenchyma (Papadopoulos et al. (supra)). To test this hypothesis, the inventors can infuse isotonic fluid into the brain parenchyma to produce vasogenic edema. Specifically, anesthetized rats are supported in a sterotaxic frame and a borosilicate glass microneedle (tip diameter ~100 μm) attached to a gas-tight 250 μL syringe is inserted into brain parenchyma. Isotonic fluid containing 0.9% saline or relaxin is infused at a rate of 0.5 μl/min for 1-6 hours. In Aqp4-/- mice, there was a significant increase in brain parenchyma water content within 1 hour (Papadopoulos et al. (supra)). At the end of the infusion period, the rats are euthanized and the brains are collected for analysis of water content and AQP4 expression in the cerebral cortex, brain stem and cerebellum. If relaxin is found to increase AQP4 expression in the treated rats, it would likely also prevent the accumulation of water in the parenchyma and reduce vasogenic edema.

Various modifications and variations of the present disclosure will be apparent to those skilled in the art without departing from the scope and spirit of the disclosure. Although the disclosure has been described in connection with specific preferred embodiments, it should be understood that the claims should not be unduly limited to such specific embodiments. Indeed, various modifications of the described modes for carrying out the disclosure, which are understood by those skilled in the art are intended to be within the scope of the claims.

What is claimed is:

1. A method of treating nephrogenic diseases of water imbalance in a human by administering purified, recombinant or synthetic H1, H2 or H3 human relaxin in an amount sufficient to increase aquaporin-4 expression in the kidney, wherein the increased expression of aquaporin-4 promotes movement of water out of the nephron filtrate and into the blood and results in a reduction of plasma osmolality.

2. The method of claim 1, wherein aquaporin-4 expression is aquaporin-4 gene expression.

3. The method of claim 1, wherein aquaporin-4 expression is aquaporin-4 protein expression.

4. The method of claim 1, wherein the nephrogenic disease of water imbalance is nephrogenic diabetes insipidus.

* * * * *